United States Patent
Yuan et al.

(10) Patent No.: US 12,040,094 B2
(45) Date of Patent: Jul. 16, 2024

(54) ARTIFICIAL INTELLIGENCE-BASED METHODS FOR EARLY DRUG DISCOVERY AND RELATED TRAINING METHODS

(71) Applicant: University of Central Florida Research Foundation, Inc., Orlando, FL (US)

(72) Inventors: Jiann-Shiun Yuan, Winter Springs, FL (US); Debopam Chakrabarti, Winter Springs, FL (US); Milad Salem, Orlando, FL (US); Arash Keshavarzi Arshadi, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 986 days.

(21) Appl. No.: 17/012,523

(22) Filed: Sep. 4, 2020

(65) Prior Publication Data
US 2021/0065913 A1    Mar. 4, 2021

Related U.S. Application Data

(60) Provisional application No. 62/895,559, filed on Sep. 4, 2019.

(51) Int. Cl.
*G16H 50/70* (2018.01)
*G06N 3/08* (2023.01)
(Continued)

(52) U.S. Cl.
CPC .......... *G16H 50/70* (2018.01); *G06N 3/08* (2013.01); *G16H 10/40* (2018.01); *G16H 50/20* (2018.01); *G16H 70/40* (2018.01)

(58) Field of Classification Search
CPC ........ G16H 50/70; G16H 10/40; G16H 50/20; G16H 70/40; G06N 3/08
See application file for complete search history.

(56) References Cited

U.S. PATENT DOCUMENTS

| | | | |
|---|---|---|---|
| 7,058,616 B1 * | 6/2006 | Larder .................. | G16B 20/20 435/5 |
| 11,587,646 B2 * | 2/2023 | Colby .................. | G06N 3/042 |

(Continued)

OTHER PUBLICATIONS

Zhou Z, Li X. Graph convolution: A high-order and adaptive approach. arXiv preprint arXiv:1706.09916. Jun. 29, 2017. (Year: 2017).*

(Continued)

*Primary Examiner* — Oluwatosin Alabi
(74) *Attorney, Agent, or Firm* — Meunier Carlin & Curcman LLC

(57) ABSTRACT

An example method for training a graph convolutional neural network (GCNN) configured for virtual screening of molecules for drug discovery is described herein. The method can include receiving a first data set including a plurality of molecules, and training the GCNN to initialize one or more parameters of the GCNN using the first data set. The method can also include receiving a second data set including a plurality of molecules and respective inhibition rates for a disease, and training the GCNN to refine the one or more parameters of the GCNN using the second data set. The molecules in the first and second data sets can be expressed in a computer-readable format. An example method for virtually screening molecules on *Plasmodium falciparum* (*P. falciparum*) is also described herein.

20 Claims, 29 Drawing Sheets

(51) Int. Cl.
      *G16H 10/40*      (2018.01)
      *G16H 50/20*      (2018.01)
      *G16H 70/40*      (2018.01)

(56) References Cited

U.S. PATENT DOCUMENTS

| | | | | |
|---|---|---|---|---|
| 11,727,282 B2* | 8/2023 | Feinberg | ............... | G06N 3/048 706/21 |
| 11,791,018 B1* | 10/2023 | Kolouri | .................. | G06N 3/084 702/27 |

OTHER PUBLICATIONS

Cho H, Choi IS. Three-dimensionally embedded graph convolutional network (3dgcn) for molecule interpretation. arXiv preprint arXiv:1811.09794. Nov. 24, 2018. (Year: 2018).*
Biswas S, Kuznetsov G, Ogden PJ, Conway NJ, Adams RP, Church GM. Toward machine-guided design of proteins. BioRxiv. Jun. 2, 2018:337154. (Year: 2018).*
Vu NA, Duy PT, Ly LT. Agraph convolution-based classification model for identifying anticancer metabolites from traditional vietnamese herbal medicine database. InProceedings of the 2nd International Conference on Machine Learning and Soft Computing Feb. 2, 2018 (pp. 122-126). (Year: 2018).*
Spier N, Nekolla S, Rupprecht C, Mustafa M, Navab N, Baust M. Classification of polar maps from cardiac perfusion imaging with graph-convolutional neural networks. Scientific reports. May 20, 2019;9(1):7569. (Year: 2019).*
Wang M, El-Fiqi H, Hu J, Abbass HA. Convolutional neural networks using dynamic functional connectivity for EEG-based person identification in diverse human states. IEEE Transactions on Information Forensics and Security. May 16, 2019;14(12):3259-72. (Year: 2019).*
Cai, C., Guo, P., Zhou, Y., Zhou, J., Wang, Q., Zhang, F., Fang, J. and Cheng, F., 2019. Deep learning-based prediction of drug-induced cardiotoxicity. Journal of chemical information and modeling, 59(3), pp. 1073-1084. (Year: 2019).*
"DeepChem About." 2019. [Online]. Available: https://deepchem.io/about.html [Accessed: Jun. 18, 2019].
Adams, Christopher P., and Van V. Brantner. "Estimating the cost of new drug development: is it really $802 million?" Health affairs 25.2 (2006): 420-428.
Altae-Tran, Han, et al. "Low data drug discovery with one-shot learning." ACS central science 3.4 (2017): 283-293.
Arshadi, Arash Keshavarzi, et al. "DeepMalaria: Artificial Intelligence Driven Discovery of Potent Antiplasmodials." Frontiers in pharmacology 10 (2020): 1526.
Ashcroft, Margaret, Yoichi Taya, and Karen H. Vousden. "Stress signals utilize multiple pathways to stabilize p53." Molecular and cellular biology 20.9 (2000): 3224-3233.
Baniecki, Mary Lynn, et al., "High-throughput Plasmodium falciparum growth assay for malaria drug discovery." Antimicrobial agents and chemotherapy 51.2 (2007): 716-723. https://doi.org/10.1128/AAC.01144-06.
Baugh, Evan H., et al. "Why are there hotspot mutations in the TP53 gene in human cancers?" Cell Death & Differentiation 25.1 (2018): 154-160.
Ben-David, Shai, et al. "Analysis of representations for domain adaptation." Advances in neural information processing systems. In Advances in NEURAL Information Processing Systems; The MIT Press: Cambridge, MA, USA, 2007; pp. 137-144.
Bjerrum, Esben Jannik. 2017. "SMILES Enumeration as Data Augmentation for Neural Network Modeling of Molecules," March. http://arxiv.org/abs/1703.07076.
Boumi, Shahab, Adan Vela, and Jacquelyn Chini. "Quantifying the relationship between student enrollment patterns and student performance." arXiv preprint arXiv:2003.10874 (2020).

Brabletz, Thomas, et al. "Migrating cancer stem cells-an integrated concept of malignant tumour progression." Nature Reviews Cancer 5.9 (2005): 744-749.
Bray, F., et al., "Global cancer statistics 2018: GLOBOCAN estimates of incidence and mortality worldwide for 36 cancers in 185 countries." CA Cancer J. Clin. 2018, 68, 394-424.
Carnero, Amancio. "High throughput screening in drug discovery." Clinical and Translational Oncology 8.7 (2006): 482-490.
Chen, Hongming, et al. "The rise of deep learning in drug discovery." Drug discovery today 23.6 (2018): 1241-1250. https://doi.org/10.1016/J.DRUDIS.2018.01.039.
Ching, Travers, et al. "Opportunities and obstacles for deep learning in biology and medicine." Journal of The Royal Society Interface 15.141 (2018): 20170387. https://doi.org/10.1098/rsif.2017.0387.
Choi, Kihang, and Andrew D. Hamilton. "Macrocyclic anion receptors based on directed hydrogen bonding interactions." Coordination chemistry reviews 240.1-2 (2003): 101-110. https://doi.org/10.1016/S0010-8545(02)00305-3.
Coley, Connor W., et al. "A graph-convolutional neural network model for the prediction of chemical reactivity." Chemical science 10.2 (2019): 370-377.
Cowell, Annie N., and Elizabeth A. Winzeler. "The genomic architecture of antimalarial drug resistance." Briefings in functional genomics 18.5 (2019): 314-328. https://doi.org/10.1093/bfgp/elz008.
Croce, Carlo M. "Oncogenes and cancer." New England journal of medicine 358.5 (2008): 502-511.
DeepChem, "DeepChem," 2019. [Online]. Available: https://deepchem.io/index.html. [Accessed: Jun. 18, 2019].
Devlin, Jacob, et al. "Bert: Pre-training of deep bidirectional transformers for language understanding." arXiv preprint arXiv:1810.04805 (2018). https://github.com/tensorflow/tensor2tensor.
Doan, Minh, and Anne E. Carpenter. "Leveraging machine vision in cell-based diagnostics to do more with less." Nature materials 18.5 (2019): 414-18. https://doi.org/10.1038/s41563-019-0339-y.
Dougherty, Patrick G., Ziqing Qian, and Dehua Pei. "Macrocycles as protein-protein interaction inhibitors." Biochemical Journal 474.7 (2017): 1109-1125. https://doi.org/10.1042/BCJ20160619.
Driggers, Edward M., et al. "The exploration of macrocycles for drug discovery—an underexploited structural class." Nature Reviews Drug Discovery 7.7 (2008): 608-624. https://doi.org/10.1038/nrd2590.
Duvenaud, David K., et al. "Convolutional networks on graphs for learning molecular fingerprints." Advances in neural information processing systems. 2015. https://dash.harvard.edu/handle/1/24873720. 28 (NIPS 2015), Montreal, Canada, Dec. 7-12, 2015: 2215-2223.
Ermert, Philipp. "Design, properties and recent application of macrocycles in medicinal chemistry." CHIMIA International Journal for Chemistry 71.10 (2017): 678-702. https://doi.org/10.2533/chimia.2017.678.
Fairhurst, Rick M, et al., "Artemisinin-Resistant Plasmodium Falciparum Malaria," Microbiol Spectr. Jun. 2016; 4(3) doi:10.1128/microbiolspec. E110-0013-2016.
Fawaz, H.I.et al., "Transfer learning for time series classification." In Proceedings of the 2018 IEEE International Conference on Big Data (Big Data), Zurich, Switzerland Seattle, WA, USA, Dec. 10-13, 2018; pp. 1367-1376.
Fischer, B., et al., "Increasing Diversity in In-silico Screening with Target Flexibility". In Computational Life Sciences; Springer: Berlin/Heidelberg, Germany, 2005; pp. 186-197.
Frankle, Jonathan, and Michael Carbin. "The lottery ticket hypothesis: Finding sparse, trainable neural networks." arXiv preprint arXiv:1803.03635 (2018).
Gamo, Francisco-Javier, et al. "Thousands of chemical starting points for antimalarial lead identification." Nature 465.7296 (2010): 305-310.
Gimeno, Aleix, et al. "The light and dark sides of virtual screening: what is there to know?" International Journal of Molecular Sciences 20.6 (2019): 1375.
Giordanetto, Fabrizio, and Jan Kihlberg. "Macrocyclic drugs and clinical candidates: what can medicinal chemists learn from their

(56) References Cited

OTHER PUBLICATIONS properties?" Journal of medicinal chemistry 57.2 (2014): 278-295. https://doi.org/10.1021/jm400887j.

Goh, Amanda M., Cynthia R. Coffill, and David P. Lane. "The role of mutant p53 in human cancer." The Journal of pathology 223.2 (2011): 116-126.

Guimaraes, Gabriel Lima, et al. "Objective-reinforced generative adversarial networks (ORGAN) for sequence generation models." arXiv preprint arXiv:1705.10843, 2017. http://arxiv.org/abs/1705.10843.

Gupta, Manish K., Swati Gupta, and Ravindra K. Rawal. "Impact of artificial neural networks in QSAR and computational modeling." Artificial Neural Network for Drug Design, Delivery and Disposition. Academic Press, 2016. 153-179. https://doi.org/10.1016/B978-0-12-801559-9.00008-9.

Hanahan, Douglas, and Robert A. Weinberg. "Hallmarks of cancer: the next generation." cell 144.5 (2011): 646-674.

Hert, Jérôme, et al. "Comparison of fingerprint-based methods for virtual screening using multiple bioactive reference structures." Journal of chemical information and computer sciences 44.3 (2004): 1177-1185.

Hu, Weihua, et al. "Strategies for Pre-training Graph Neural Networks." Eighth International Conference on Learning Representations (ICLR), Apr. 26-May 1, 2020.

Huang, Gao, Zhuang Liu, Laurens van der Maaten, and Kilian Q. Weinberger. Aug. 2016. "Densely Connected Convolutional Networks," 9 pages.

Huang, Min, et al. "Molecularly targeted cancer therapy: some lessons from the past decade." Trends in pharmacological sciences 35.1 (2014): 41-50.

Jiang, Fei, et al. "Artificial intelligence in healthcare: past, present and future." Stroke and vascular neurology 2.4 (2017): 230-243. https://doi.org/10.1136/svn-2017-000101.

Kadurin, Artur, et al. "The cornucopia of meaningful leads: Applying deep adversarial autoencoders for new molecule development in oncology." Oncotarget 8.7 (2017): 10883. https://doi.org/10.18632/oncotarget.14073.

Kearnes, Steven, et al. "Molecular graph convolutions: moving beyond fingerprints." Journal of computer-aided molecular design 30.8 (2016): 595-608. https://doi.org/10.1007/s10822-016-9938-8.

Koehn, Frank E., and Guy T. Carter. "The evolving role of natural products in drug discovery." Nature reviews Drug discovery 4.3 (2005): 206-220. https://doi.org/10.1038/nrd1657.

Korotcov, Alexandru, et al. "Comparison of deep learning with multiple machine learning methods and metrics using diverse drug discovery data sets." Molecular pharmaceutics 14.12 (2017): 4462-4475.

Lane, David P. "Cancer. p53, guardian of the genome." Nature 358 (1992): 15-16.

Leelananda, Sumudu P., and Steffen Lindert. "Computational methods in drug discovery." Beilstein journal of organic chemistry 12.1 (2016): 2694-2718. https://doi.org/10.3762/bjoc.12.267.

Li, Jesse W-H., and John C. Vederas. "Drug discovery and natural products: end of an era or an endless frontier?" Science 325.5937 (2009): 161-165. https://doi.org/10.1126/science.1168243.

Liu, Ke, et al. "Chemi-net: a graph convolutional network for accurate drug property prediction." arXiv preprint arXiv:1803.06236, 2018, 36 pages.

Liu, S. "Exploration on Deep Drug Discovery: Representation and Learning; Computer Science", University of Wisconsin-Madison: Madison, WI, USA, 2018. 89 pages.

Liu, S., et al., "End-to-end multi-task learning with attention." In Proceedings of the IEEE Conference on Computer Vision and Pattern Recognition, Long Beach, CA, USA, Jun. 16-20, 2019; pp. 1871-1880.

Liu, Shengchao, et al. "Practical model selection for prospective virtual screening." Journal of chemical information and modeling 59.1 (2018): 282-293.

Mallinson, Jamie, and Ian Collins. "Macrocycles in new drug discovery." Future medicinal chemistry 4.11 (2012): 1409-1438. https://doi.org/10.4155/fmc.12.93.

Mayr, Andreas, et al. "DeepTox: toxicity prediction using deep learning." Frontiers in Environmental Science 3 (2016): 80. https://doi.org/10.3389/fenvs.2015.00080.

Mayr, Andreas, et al. "Large-scale comparison of machine learning methods for drug target prediction on ChEMBL." Chemical science 9.24 (2018): 5441-5451. https://doi.org/10.1039/C8SC00148K.

Meiseles, Amiel, and Lior Rokach. "Source Model Selection for Deep Learning in the Time Series Domain." IEEE Access 8 (2020): 6190-6200.

Miljković, Filip, et al., "Machine learning models for accurate prediction of kinase inhibitors with different binding modes." Journal of medicinal chemistry (Pub date: Aug. 2019), J. Med. Chem. 2020, 63, 16, 8738-8748. https://doi.org/10.1021/acs.jmedchem.9b00867.

Minnich, Amanda J., et al. "AMPL: A Data-Driven Modeling Pipeline for Drug Discovery." Journal of Chemical Information and Modeling 60.4 (2020): 1955-1968.

Mohs, R.C.; Greig, N.H. Drug discovery and development: Role of basic biological research. Alzheimer's Dement. (N. Y.) 2017, 3, 651-657.

Nassif, Ali Bou, et al. "Speech recognition using deep neural networks: A systematic review." IEEE Access 7 (2019): 19143-19165.

Oren, M. "Decision making by p53: life, death and cancer." Cell Death & Differentiation 10.4 (2003): 431-442.

Parhizgar, Arezoo Rafiee, and Azar Tahghighi. 2017. "Introducing New Antimalarial Analogues of Chloroquine and Amodiaquine: A Narrative Review." Iranian Journal of Medical Sciences 42 (2): 115.

Parrales, Alejandro, and Tomoo Iwakuma. "Targeting oncogenic mutant p53 for cancer therapy." Frontiers in oncology 5 (2015): 288.

Perez-Castillo, Yunierkis, et al. "A desirability-based multi objective approach for the virtual screening discovery of broad-spectrum anti-gastric cancer agents." PloS one 13.2 (2018): e0192176.

Pérez-Sianes, Javier, Horacio Pérez-Sánchez, and Fernando Díaz. 2016. "Virtual Screening: A Challenge for Deep Learning." 13-22. Springer, Cham. https://doi.org/10.1007/978-3-319-40126-3_2.

Pirhaji, Leila, et al. "Revealing disease-associated pathways by network integration of untargeted metabolomics." Nature methods 13.9 (2016): 770-776. https://doi.org/10.1038/nmeth.3940.

Popova, Mariya, Olexandr Isayev, and Alexander Tropsha. "Deep reinforcement learning for de novo drug design." Science advances 4.7 (2018): eaap7885.

Powell, Emily, David Piwnica-Worms, and Helen Piwnica-Worms. "Contribution of p53 to metastasis." Cancer discovery 4.4 (2014): 405-414.

PubChem Database. 2019. "National Center for Biotechnology Information." 2019. https://pubchem.ncbi.nlm.nih.gov/bioassay/686979.

PubChem Database. Source=NCGC AID=904. 2007. Available online: https://pubchem.ncbi.nlm.nih.gov/bioassay/904 (accessed on May 18, 2020).

Rajpurkar, Pranav, Awni Y. Hannun, Masoumeh Haghpanahi, Codie Bourn, and Andrew Y. Ng. 2017. "Cardiologist-Level Arrhythmia Detection with Convolutional Neural Networks," July. http://arxiv.org/abs/1707.01836.

Ramsundar, Bharath, et al., 2015. "Massively Multitask Networks for Drug Discovery," February. 27 pages. http://arxiv.org/abs/1502.02072.

Ramsundar, Bharath., Peter. Eastman, Patrick. Walters, and Vijay. Pande. 2019. Deep Learning for the Life Sciences: Applying Deep Learning to Genomics, Microscopy, Drug Discovery): Chapter 3. Machine Learning with DeepChem. 62 pages.

Reddy, Sandeep, John Fox, and Maulik P. Purohit. "Artificial intelligence-enabled healthcare delivery." Journal of the Royal Society of Medicine 112.1 (2019): 22-28. https://doi.org/10.1177/0141076818815510.

Research and Markets, "Global $1.04 Billion Anti-Malarial Drugs Market to 2027". Dated Dec. 4, 2018. Available on-line at: https://www.prnewswire.com/news-releases/global-1-04-billion-anti-malarial-drugs-market-to-2027---focus-on-anti-malarial-activity-tissue-

(56) References Cited

OTHER PUBLICATIONS schizonticides-blood-schizonticides-gametocytocides--sporontocides-300759832.html#:~:text=The%20Global%20Anti%2DMalarial%20Drugs,by%20the%20end%20of%202027.&text=Further%2C%20the%20market%20is%20expected,USD%20222.8%20Million%20in%202016.

Riss, Terry L., et al. "Cell viability assays." Assay Guidance Manual [Internet]. Eli Lilly & Company and the National Center for Advancing Translational Sciences, 2016.

Roberts, Bracken F., et al. "Current Opinion: 4-Nitro styrylquinoline is an antimalarial inhibiting multiple stages of Plasmodium falciparum asexual life cycle." International Journal for Parasitology: Drugs and Drug Resistance 7.1 (2017): 120-129. https://doi.org/10.1016/j.ijpddr.2017.02.002.

Rogers, David, and Mathew Hahn. "Extended-connectivity fingerprints." Journal of chemical information and modeling 50.5 (2010): 742-754. https://doi.org/10.1021/ci100050t.

Sánchez-Rodríguez, Aminael, et al. "From flamingo dance to (desirable) drug discovery: a nature-inspired approach." Drug discovery today 22.10 (2017): 1489-1502.

Schneider, Gisbert. "Automating drug discovery." Nature Reviews Drug Discovery 17.2 (2018): 97-113. https://doi.org/10.1038/nrd.2017.232.

Selwood, David L "Macrocycles, the Edge of Drug-Likeness Chemical Space or Goldilocks Zone?" Chemical Biology & Drug Design 2017, 89 (2): 164-68. https://doi.org/10.1111/cbdd.12922.

Shoichet, Brian K. "Virtual screening of chemical libraries." Nature 432.7019 (2004): 862-865. https://doi.org/10.1038/nature03197.

Smyth, Mark J., Gavin P. Dunn, and Robert D. Schreiber. "Cancer immunosurveillance and immunoediting: the roles of immunity in suppressing tumor development and shaping tumor immunogenicity." Advances in immunology 90 (2006): 1-50.

Spangenberg, Thomas, et al. "The open access malaria box: a drug discovery catalyst for neglected diseases." PloS one 8.6 (2013): e62906. https://doi.org/10.1371/journal.pone.0062906.

Sun, Q, et al., "Meta-transfer learning for few-shot learning." In Proceedings of the IEEE Conference on Computer Vision and Pattern Recognition, Long Beach, CA, USA, Jun. 16-20, 2019; pp. 403-412.

Swamidass, S. Joshua, et al. "Influence relevance voting: an accurate and interpretable virtual high throughput screening method." Journal of chemical information and modeling 49.4 (2009): 756-766.

Swinney, D C. "Phenotypic vs. Target-Based Drug Discovery for First-in-Class Medicines." Clinical Pharmacology & Therapeutics (2013) 93 (4): 299-301. https://doi.org/10.1038/clpt.2012.236.

Torng, Wen, and Russ B. Altman. "Graph convolutional neural networks for predicting drug-target interactions." Journal of Chemical Information and Modeling 59.10 (2019): 4131-4149.

Vossen, Matthias G., et al. "The SYBR Green I malaria drug sensitivity assay: performance in low parasitemia samples." The American journal of tropical medicine and hygiene 82.3 (2010): 398-401. https://doi.org/10.4269/ajtmh.2010.09-0417.

Wainberg, Michael, et al. "Deep learning in biomedicine." Nature biotechnology 36.9 (2018): 829-838. https://doi.org/10.1038/nbt.4233.

Wallach, Izhar, Michael Dzamba, and Abraham Heifets. "AtomNet: A Deep Convolutional Neural Network for Bioactivity Prediction in Structure-Based Drug Discovery," (2015) 1-11.

Wang, Li-Hui, et al. "Loss of tumor suppressor gene function in human cancer: An overview." Cellular Physiology and Biochemistry 51.6 (2018): 2647-2693.

Wang, Mei, and Weihong Deng. "Deep visual domain adaptation: A survey." Neurocomputing 312 (2018): 135-153.

Wang, Qian, and Dinggang Shen. "Computational Medicine: A Cybernetic Eye for Rare Disease." Nature Biomedical Engineering 1 (2): (2017) 0032. https://doi.org/10.1038/s41551-017-0032.

Willcox, Merlin L., and Gerard Bodeker. "Traditional herbal medicines for malaria." Bmj 329.7475 (2004): 1156-1159. https://doi.org/10.1136/bmj.329.7475.1156.

Wilson, Danny W., et al. "Defining the timing of action of antimalarial drugs against Plasmodium falciparum." Antimicrobial agents and chemotherapy 57.3 (2013): 1455-1467. https://doi.org/10.1128/AAC.01881-12.

World Health Organization. 2018. "WHO." 2018.

Wu, Zhenqin, et al., "MoleculeNet: A Benchmark for Molecular Machine Learning." Chemical Science (2018) 9 (2): 513-30. https://doi.org/10.1039/C7SC02664A.

Yabroff, K.R.; Warren, J.L.; Brown, M.L. Costs of cancer care in the USA: A descriptive review. Nat. Clin. Pract. Oncol. 2007, 4, 643-656.

Zhang, H.; Koniusz, P. Model Selection for Generalized Zero-Shot Learning. In Computer Vision—ECCV 2018 Workshops; Springer International Publishing: Cham, Switzerland, 2019; pp. 198-204.

Zhang, H.; Koniusz, P. Zero-Shot Kernel Learning. In Proceedings of the 2018 IEEE/CVF Conference on Computer Vision and Pattern Recognition, Salt Lake City, UT, USA, Jun. 18-22, 2018; pp. 7670-7679.

Zhang, Hongguang, and Piotr Koniusz. "Power normalizing second-order similarity network for few-shot learning." 2019 IEEE Winter Conference on Applications of Computer Vision (WACV). pp. 1185-1193.

Zhang, Ke, et al. "Multiple feature reweight densenet for image classification." IEEE Access 7 (2019): 9872-9880.

Zhang, Wen, et al. "Drug side effect prediction through linear neighborhoods and multiple data source integration." 2016 IEEE international conference on bioinformatics and biomedicine (BIBM). IEEE, 2016, 427-34. https://doi.org/10.1109/BIBM.2016.7822555.

Zhavoronkov, Alex, et al. "Artificial intelligence for aging and longevity research: Recent advances and perspectives." Ageing research reviews 49 (2019): 49-66. https://doi.org/10.1016/J.ARR.2018.11.003.

Zhuang, Fuzhen, et al. "Transfer Learning Toolkit: Primers and Benchmarks." arXiv preprint arXiv:1911.08967 (2019).

International Search Report and Written Opinion issued in PCT/US2023/060385, mailed Jul. 13, 2023, 12 pages.

Kyrollos et al., RPmirDIP: Reciprocal Perspective improves miRNA targeting prediction, Scientific Reports, vol. 10, Article No. 11770, Jul. 16, 2020, pp. 1-13.

Azzaoui et al., Discovery of Small Molecule Drugs Targeting the Biogenesis of microRNA-155 for the Treatment of Systemic Lupus Erythematosus, CHIMIA International Journal for Chemistry, vol. 74, No. 10, Oct. 28, 2020, pp. 798-802.

* cited by examiner

Table 1. Classification Categories.

|                      | Truly Active | Truly Inactive |
|----------------------|--------------|----------------|
| Predicted as Active  | TP           | FP             |
| Predicted as Inactive| FN           | TN             |

FIG. 7

Table 2. Finalized hyper-parameters from grid search.

| Hyper-Parameter   | Optimum Value | Hyper-Parameter | Optimum Value |
|-------------------|---------------|-----------------|---------------|
| # of Conv. Layers | 3             | Dropout         | 0             |
| Conv. Layer Sizes | 64, 64, 64    | Learning Rate   | 0.0001        |
| # of Neurons      | 256           | Batch Size      | 128           |

FIG. 8

Table 3. Results of the trained model.

|  | # of Active | TP | Accuracy | Recall |
|---|---|---|---|---|
| Validation Dataset | 112 | 81 | 60.06 | 72.32 |
| Test Dataset | 49 | 43 | 44.13 | 87.75 |

FIG. 9

Table 4. Comparison of different models on test dataset.

|  | Featurization | Accuracy | Recall | ROC-AUC |
|---|---|---|---|---|
| Random Forest | ECFP | 14.08 | 89.79 | 0.51 |
| DeepMalaria without Transfer Learning | GraphConv | 33.46 | 77.55 | 0.55 |
| DeepMalaria | GraphConv | 44.13 | 87.75 | 0.69 |

FIG. 10

Source data information.

| Dataset | Data Type | Number of Tasks | Number of Compounds |
|---------|-----------|-----------------|---------------------|
| PCBA    | SMILES    | 124             | 437,929             |
| MUV     |           | 17              | 93,087              |
| HIV     |           | 1               | 41,127              |
| BACE    |           | 1               | 1513                |
| Tox21   |           | 12              | 7831                |
| SIDER   |           | 27              | 1427                |

*FIG. 11*

Target data information.

| Dataset  | Data Type | Number of Tasks | Number of Compounds | Number of Active Compounds |
|----------|-----------|-----------------|---------------------|----------------------------|
| PCBA-904 | SMILES    | 1               | 437,929             | 528                        |

*FIG. 12*

Baseline results for the cancer candidate prediction models.

| Task | Partition | Accuracy | Recall | ROC-AUC |
|---|---|---|---|---|
| PCBA-904 | Validation | 90.96 | 57.14 | 0.7846 |
| PCBA-904 | Test | 89.66 | 25 | 0.7322 |

FIG. 14

Best performing source models for transfer learning on the target test dataset.

| Source Dataset | Source Task | Target Task | Accuracy | Recall | BEDROC (Alpha = 1) | ROC-AUC | Improvement |
|---|---|---|---|---|---|---|---|
| PCBA | PCBA-651635 | PCBA-904 | 72.49 | 100 | 0.779 | 0.918 | 0.186 |
| Tox21 | NR-AhR | | 82.11 | 75 | 0.678 | 0.889 | 0.158 |
| SIDER | Ear and labyrinth disorders | | 73.56 | 87.5 | 0.392 | 0.882 | 0.150 |
| MUV | MUV-832 | | 81.68 | 75 | 0.677 | 0.871 | 0.138 |
| HIV | HIV | | 83.05 | 37.5 | 0.505 | 0.761 | 0.029 |
| BACE | BACE | | 92.31 | 12.5 | 0.099 | 0.747 | 0.005 |
| PCBA [18] | PCBA-903 | | - | - | - | 0.81 | - |

FIG. 17

Evaluation of each pre-trained model ranking approach.

| Ranking Approach | Correlation to Improvement | MRR (Top 10) | Correct Predictions (Top 10) |
|---|---|---|---|
| IDS [38] | −0.03 | 0.017 | 0 |
| MSC [4] | 0.05 | 0.009 | 0 |
| Zero-Shot (Ours) | 0.22 | 0.063 | 2 |

*FIG. 22*

Details of the common architecture and hyper-parameters.

| Parameter | Values | Parameter | Value |
|---|---|---|---|
| Number of conv. layers | 3 | Size of conv. layers | 64 |
| Number of neurons | 256 | Learning rate | 0.0001 |
| Dropout | 0 | Batch size | 128 |

FIG. 30

Source tasks and their referred number within the figures, part 1.

| Task | Number | Task | Number | Task | Number | Task | Number |
|---|---|---|---|---|---|---|---|
| BACE | 1 | PCBA-885 | 36 | PCBA-485281 | 71 | PCBA-588590 | 106 |
| HIV | 2 | PCBA-887 | 37 | PCBA-485290 | 72 | PCBA-588591 | 107 |
| MUV-466 | 3 | PCBA-891 | 38 | PCBA-485294 | 73 | PCBA-588795 | 108 |
| MUV-733 | 4 | PCBA-899 | 39 | PCBA-485297 | 74 | PCBA-588855 | 109 |
| MUV-737 | 5 | PCBA-912 | 40 | PCBA-485313 | 75 | PCBA-602179 | 110 |
| MUV-810 | 6 | PCBA-914 | 41 | PCBA-485314 | 76 | PCBA-1460 | 111 |
| MUV-832 | 7 | PCBA-915 | 42 | PCBA-485341 | 77 | PCBA-602233 | 112 |
| MUV-846 | 8 | PCBA-1479 | 43 | PCBA-1454 | 78 | PCBA-602310 | 113 |
| MUV-852 | 9 | PCBA-925 | 44 | PCBA-485349 | 79 | PCBA-602313 | 114 |
| MUV-858 | 10 | PCBA-926 | 45 | PCBA-485353 | 80 | PCBA-602332 | 115 |
| MUV-859 | 11 | PCBA-927 | 46 | PCBA-485360 | 81 | PCBA-624170 | 116 |
| MUV-548 | 12 | PCBA-928 | 47 | PCBA-485364 | 82 | PCBA-624171 | 117 |
| MUV-600 | 13 | PCBA-995 | 48 | PCBA-485367 | 83 | PCBA-624173 | 118 |
| MUV-644 | 14 | PCBA-1631 | 49 | PCBA-492947 | 84 | PCBA-624202 | 119 |
| MUV-652 | 15 | PCBA-1634 | 50 | PCBA-493208 | 85 | PCBA-624246 | 120 |
| MUV-689 | 16 | PCBA-1688 | 51 | PCBA-504327 | 86 | PCBA-624287 | 121 |
| MUV-692 | 17 | PCBA-1721 | 52 | PCBA-504332 | 87 | PCBA-1461 | 122 |
| MUV-712 | 18 | PCBA-2100 | 53 | PCBA-504333 | 88 | PCBA-624288 | 123 |
| MUV-713 | 19 | PCBA-2101 | 54 | PCBA-1457 | 89 | PCBA-624291 | 124 |
| PCBA-1030 | 20 | PCBA-2147 | 55 | PCBA-504339 | 90 | PCBA-624296 | 125 |
| PCBA-1469 | 21 | PCBA-1379 | 56 | PCBA-504444 | 91 | PCBA-624297 | 126 |
| PCBA-720553 | 22 | PCBA-2242 | 57 | PCBA-504466 | 92 | PCBA-624417 | 127 |
| PCBA-720579 | 23 | PCBA-2326 | 58 | PCBA-504467 | 93 | PCBA-651635 | 128 |
| PCBA-720580 | 24 | PCBA-2451 | 59 | PCBA-504706 | 94 | PCBA-651644 | 129 |
| PCBA-720707 | 25 | PCBA-2517 | 60 | PCBA-504842 | 95 | PCBA-651768 | 130 |
| PCBA-720708 | 26 | PCBA-2528 | 61 | PCBA-504845 | 96 | PCBA-651965 | 131 |
| PCBA-720709 | 27 | PCBA-2546 | 62 | PCBA-504847 | 97 | PCBA-652025 | 132 |
| PCBA-720711 | 28 | PCBA-2549 | 63 | PCBA-504891 | 98 | PCBA-1468 | 133 |
| PCBA-743255 | 29 | PCBA-2551 | 64 | PCBA-540276 | 99 | PCBA-652104 | 134 |
| PCBA-743266 | 30 | PCBA-2662 | 65 | PCBA-1458 | 100 | PCBA-652105 | 135 |
| PCBA-875 | 31 | PCBA-2675 | 66 | PCBA-540317 | 101 | PCBA-652106 | 136 |
| PCBA-1471 | 32 | PCBA-1452 | 67 | PCBA-588342 | 102 | PCBA-686970 | 137 |
| PCBA-881 | 33 | PCBA-2676 | 68 | PCBA-588453 | 103 | PCBA-686978 | 138 |
| PCBA-883 | 34 | PCBA-411 | 69 | PCBA-588456 | 104 | PCBA-686979 | 139 |
| PCBA-884 | 35 | PCBA-463254 | 70 | PCBA-588579 | 105 | PCBA-720504 | 140 |

FIG. 31

Source tasks and their referred number within the figures, part 2.

| Task | Number | Task | Number | Task | Number | Task | Number |
|---|---|---|---|---|---|---|---|
| PCBA-720532 | 141 | Metabolism and nutrition disorders | 152 | Vascular disorders | 163 | SR-p53 | 174 |
| PCBA-720542 | 142 | Musculoskeletal and connective tissue disorders | 153 | "Neoplasms benign, malignant and unspecified (incl cysts and polyps)" | 164 | NR-AR | 175 |
| PCBA-720553 | 143 | Nervous system disorders | 154 | "Pregnancy, puerperium and perinatal conditions" | 165 | NR-AR-LBD | 176 |
| "Congenital, familial and genetic disorders" | 144 | "Injury, poisoning and procedural complications" | 155 | "Respiratory, thoracic and mediastinal disorders" | 166 | NR-Aromatase | 177 |
| Eye disorders | 145 | Product issues | 156 | Blood and lymphatic system disorders | 167 | NR-ER | 178 |
| Gastrointestinal disorders | 146 | Psychiatric disorders | 157 | Cardiac disorders | 168 | NR-ER-LBD | 179 |
| General disorders and administration site conditions | 147 | Renal and urinary disorders | 158 | Ear and labyrinth disorders | 169 | NR-PPAR-gamma | 180 |
| Hepatobiliary disorders | 148 | Reproductive system and breast disorders | 159 | Endocrine disorders | 170 | SR-ARE | 181 |
| Immune system disorders | 149 | Skin and subcutaneous tissue disorders | 160 | NR-AhR | 171 | SR-ATAD5 | 182 |
| Infections and infestations | 150 | Social circumstances | 161 | SR-HSE | 172 | | |
| Investigations | 151 | Surgical and medical procedures | 162 | SR-MMP | 173 | | |

*FIG. 32*

ARTIFICIAL INTELLIGENCE-BASED METHODS FOR EARLY DRUG DISCOVERY AND RELATED TRAINING METHODS

CROSS-REFERENCE TO RELATED APPLICATIONS

This application claims the benefit of U.S. provisional patent application No. 62/895,559, filed on Sep. 4, 2019, and entitled "ARTIFICIAL INTELLIGENCE-BASED METHODS FOR PREDICTING ANTIMALARIAL COMPOUNDS AND METHOD FOR TRAINING THE SAME," the disclosure of which is expressly incorporated herein by reference in its entirety.

BACKGROUND

Drug development is a long and costly process during which a drug candidate is discovered and widely tested to be both efficient and safe. This process can take an average of 12 years with billions of dollars spent per drug [1,2]. The early stages of this process involve discovery of a drug candidate which is bio-active towards the targeted disease and is non-toxic for humans. High Throughput Screening (HTS) is a conventional screening used to screen a big library of molecules for discovery of a potent scaffold. HTS, however, is very inefficient.

Conventional screening techniques such as HTS may discourage pharmaceutical companies from pursuing drug discovery. For example, malaria is one the deadliest microbes in the world, with more than 200 million new cases every year, and over 400,000 reported deaths (World Health Organization 2018). The agent of infection, *Plasmodium* spp. parasites have developed resistance against almost all currently marketed drugs and therapies including Artemisinin-based Combination Therapy (ACT) (Fairhurst and Dondorp 2016), indicating an urgent need for alternative anti-malarial (Cowell and Winzeler 2019). Cancer on the other hand, is one of the deadliest non-infectious disease worldwide. Cancer incidents in the U.S. is expected to grow 22% in 2020 compared to 2010. Therefore, there is an urgent need for new technologies to discover drugs and preventers (CDC 2018). Additionally, these compounds need to be fast-acting, show high stability and bioavailability, and be relatively inexpensive to synthesis (Parhizgar and Tahghighi 2017). Traditionally, the discovery of new compounds relies on cell-based screening (Baniecki, Wirth, and Clardy 2007) of natural or synthetic compound libraries, either with irrational or target-based approaches (Swinney 2013). HTS of either hit discovery types is often inefficient, discouraging many pharmaceutical companies from pursuing antimalarial drug discovery.

The HTS stage is one of the main bottlenecks of the drug discovery process. HTS involves purchasing a library of compounds and testing them on a targeted disease. If this process is successful, multiple molecules would be found within the library that inhibit the disease and are possible drug candidates or "hits". The main problems of this stage are its costliness and the fact that the hit rates of the libraries are often quite low. Therefore, those who perform HTS spend a considerable amount of money in order to find very few possible drug candidates. If no change is made to the costly HTS process and compounds libraries with low hit rate, the pace of malaria's resistance development could exceed that of the drug discovery process.

SUMMARY

An artificial intelligence (AI)-based approach to predict bioactive compounds for non-structural based drug discovery is described herein. For example, this AI algorithm was trained using 13,000 active compounds from available public data. The AI-based hit prediction algorithm was validated by screening a commercial library of 2,400 compounds. The validation screening experiment demonstrated that AI algorithm identified 42 of 48 hits (87.5%). Compared to traditional high throughput screening approaches, the AI algorithm performs in simulation, is much cheaper and faster, and can decrease the volume of the search space vastly. The AI algorithm described herein is the first of its kind for malaria in terms of virtual screening and is non-target based.

An example method for training a graph convolutional neural network (GCNN) configured for virtual screening of molecules for drug discovery is described herein. The method can include receiving a first data set including a plurality of molecules, and training the GCNN to initialize one or more parameters of the GCNN using the first data set. The method can also include receiving a second data set including a plurality of molecules and respective inhibition rates for a disease, and training the GCNN to refine the one or more parameters of the GCNN using the second data set. The molecules in the first and second data sets can be expressed in a computer-readable format. Additionally, the molecules in the first data set can be unrelated to the molecules in the second data set.

In some implementations, the method can optionally include defining each of the molecules in the second data set by a plurality of selected features; and converting the molecules in the second data set defined by the selected features into a plurality of respective graphs associated with each of the molecules. The step of training the GCNN to refine the one or more parameters of the GCNN can include training the GCNN to refine the one or more parameters of the GCNN using the respective graphs.

In some implementations, the selected features include a type of atom in a molecule, a degree of the atom, an implicit valence of the atom, hybridization of the atom, an aromatic property of the atom, a number of hydrogen atoms connected to the atom, or combinations thereof. Optionally, the selected features further include chirality of the molecule.

In some implementations, the method can optionally include optimizing a plurality of hyper-parameters of the GCNN. The hyper-parameters can include at least one of a number of convolution layers, a size of each convolution layer, a number of neurons in a dense layer, a dropout for each layer, a number of epochs, a learning rate, and a batch size. Optionally, the step of optimizing a plurality of hyper-parameters of the GCNN further includes: setting a plurality of respective values for each of the hyper-parameters; for each respective value, training the GCNN using a set of molecules from the second data set and testing the GCNN using a third data set including a plurality of molecules; and selecting a set of respective values for each of the hyper-parameters. The molecules in the third data set are expressed in the computer-readable format. Additionally, the set of respective values for each of the hyper-parameters optimize performance of the GCNN.

In some implementations, the method can optionally include augmenting the third data set to include additional copies of active molecules. Optionally, the third data set includes lab-validated data.

In some implementations, the computer-readable format is simplified molecular input line entry system (SMILES) notation.

In some implementations, the GCNN is configured for antimalarial drug discovery. In other implementations, the GCNN is configured for anticancer drug discovery.

Another example method for training a graph convolutional neural network (GCNN) configured for virtual screening of molecules for drug discovery is described herein. The method can include receiving a plurality of source data sets, where each of the source data sets includes a plurality of molecules. The molecules in each of the source data sets are expressed in a computer-readable format. The method can also include training a plurality of GCNNs to initialize one or more parameters of each of the GCNNs, where each of the GCNNs is trained using a respective one of the source data sets. The method can also include receiving a training data set, where the training data set includes a plurality of molecules and respective inhibition rates for a disease. The molecules in the training data set are expressed in the computer-readable format. The method can also include training each of the GCNNs to refine the one or more parameters of each of the GCNNs using the training data set.

In some implementations, the source data sets have at least one of different data sizes, different data diversity, or different biological origin.

In some implementations, the method can optionally further include ranking each of the GCNNs trained using a respective one of the source data sets based on its respective predicted performance on the training data set. For example, the step of ranking each of the GCNNs trained using a respective one of the source data sets based on its respective predicted performance on the training data set can include analyzing a respective inter-dataset similarity between each of the source data sets and the training data set. Alternatively, the step of ranking each of the GCNNs trained using a respective one of the source data sets based on its respective predicted performance on the training data set can include analyzing a respective ability of each of the GCNNs trained using a respective one of the source data sets to distinguish between active and inactive target molecules. Alternatively, the step of ranking each of the GCNNs trained using a respective one of the source data sets based on its respective predicted performance on the training data set includes testing each of the GCNNs trained using a respective one of the source data sets using a validation data set.

In some implementations, each of the GCNNs is trained using a respective one of the source data sets for more epochs than each of the GCNNs is trained using the training data set.

An example method for virtually screening molecules on *Plasmodium falciparum* (*P. falciparum*) is also described herein. The method can include providing a graph convolutional neural network (GCNN), receiving a molecule, and predicting, using the GCNN, whether the molecule inhibits *P. falciparum*. The molecule can be expressed in a computer-readable format.

In some implementations, the method can optionally include classifying the molecule as an active molecule or an inactive molecule, where the active molecule is a drug candidate for treating *P. falciparum*. Optionally, the method can further include confirming the active molecule is a drug candidate for treating *P. falciparum* using an in-vitro test.

In some implementations, the method can optionally include defining the molecule by a plurality of selected features; converting the molecule defined by the selected features into a graph; and inputting the graph into the GCNN to predict whether the molecule inhibits *P. falciparum*.

In some implementations, the selected features include a type of atom in the molecule, a degree of the atom, an implicit valence of the atom, hybridization of the atom, an aromatic property of the atom, a number of hydrogen atoms connected to the atom, or combinations thereof. Optionally, the selected features further include chirality of the molecule.

In some implementations, the GCNN include three convolution layers. Optionally, a size of each convolution layer is 64 convolutional filters. Alternatively or additionally, the GCNN optionally further includes a dense layer. Optionally, the dense layer comprises 256 neurons.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 7 is Table 1, which illustrates classification categories.

FIG. 8 is Table 2, which illustrates optimal hyper-parameters for a GCNN according to an implementation described herein.

FIG. 9 is Table 3, which illustrates results of the trained GCNN.

FIG. 10 is Table 4, which illustrates comparison of different models on the test data set. The GCNN described herein is shown as DeepMalaria (Example 1) in the table. The table also shows how transfer learning improves accuracy of the GCNN.

FIG. 11 is Table 5, which illustrates source data information (TranScreen, Example 2).

FIG. 12 is Table 6, which illustrates target data information (TranScreen, Example 2).

FIG. 14 is Table 7, which illustrates baseline results for the cancer candidate prediction models (TranScreen, Example 2).

FIG. 17 contains Table 8, which illustrates best performing source models for transfer learning on the target test dataset (TranScreen, Example 2).

FIGS. 18A-18B illustrate confusion matrix comparison between: (FIG. 18A) baseline model; (FIG. 18B) best performing model after transfer learning.

FIG. 22 is Table 9, which illustrates evaluation of each pre-trained model ranking approach.

FIGS. 24A-24B illustrate ROC-AUC curves on target test dataset for: (FIG. 24A) baseline model; (FIG. 24B) best performing model after transfer learning.

FIG. 30 is Table 10, which illustrates details of the common architecture and hyper-parameters (TranScreen, Example 2).

FIG. 31 is Table 11, which illustrates source tasks and their referred number within the figures, part 1 (TranScreen, Example 2).

FIG. 32 is Table 12, which illustrates source tasks and their referred number within the figures, part 2 (TranScreen, Example 2).

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations will be described for antimalarial drug discovery, it will become evident to those skilled in the art that the implementations are not limited thereto, but may be applicable for other drug discovery applications.

Figure 1A:
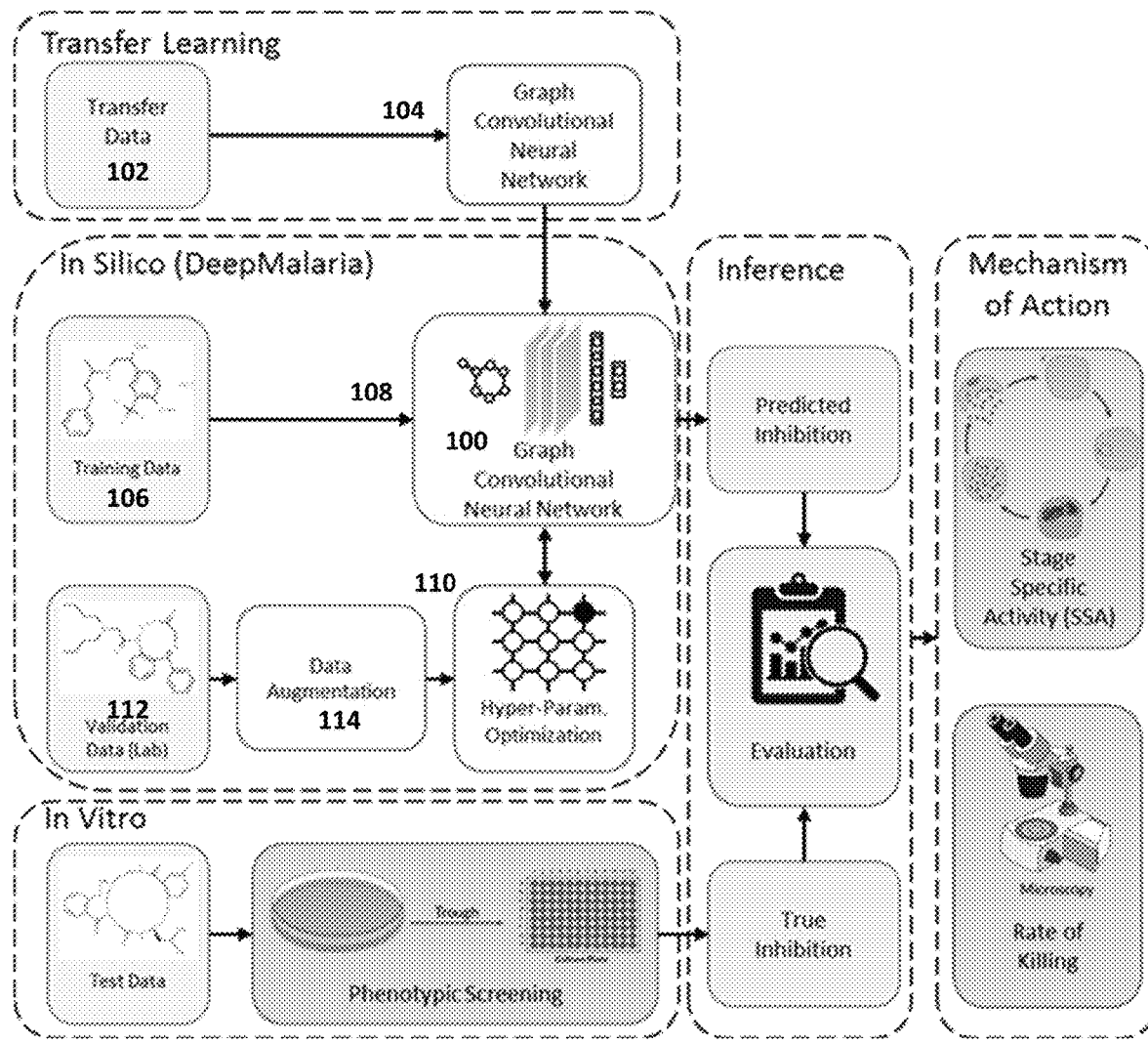
FIG. 1A is a diagram illustrating example operations for training a graph convolutional neural network (GCNN) configured for virtual screening of molecules for drug discovery according to an implementation described herein.

Referring now to FIG. 1A, an example method for training a graph convolutional neural network (GCNN) 100 configured for virtual screening of molecules for drug discovery is described. In some implementations, the GCNN can be configured for antimalarial drug discovery (see e.g., Example 1 below). It should be understood that antimalarial drug discovery is only provided as an example. This disclosure contemplates that the GCNN training method described herein may be used in other drug discovery applications including, but not limited to, discovery of anti-cancer compounds (see e.g., Example 2 below). The GCNN training method described below uses transfer learning to increase the accuracy of the GCNN. As described herein, transfer learning is beneficial in applications where the training data set is relatively small, which makes training the GCNN sensitive to the initial weights. Transfer learning, however, is new to the field of drug discovery, since transfer learning requires a large data source, while open data sources in this domain are often limited and the existing related datasets are often small in size. Additionally, the transfer learning described herein is different from transfer learning in conventional applications. For example, the transfer learning in some implementations described herein uses unrelated data, creating more opportunities and less constraint for implementing transfer learning and increasing the accuracy of any drug discovery model. Additionally, the transfer learning described herein is performed on GCNN rather than traditional artificial neural networks.

A neural network is a computing system including a plurality of interconnected neurons (e.g., also referred to as "nodes"). This disclosure contemplates that the nodes can be implemented using a computing device (e.g., a processing unit and memory as described herein). The nodes can optionally be arranged in a plurality of layers such as input layer, output layer, and one or more hidden layers. Each node is connected to one or more other nodes in the neural network. For example, each layer has a plurality of nodes, where each node is connected to all nodes in the previous layer. The nodes in a given layer are not interconnected with one another, i.e., the nodes in a given layer function independently of one another. As used herein, nodes in the input layer receive data from outside of the neural network, nodes in the hidden layer(s) modify the data between the input and output layers, and nodes in the output layer provide the results. Each node is configured to receive an input, implement a function (e.g., sigmoid function or rectified linear unit (ReLU) function), and provide an output in accordance with the function. Additionally, each node is associated with a respective weight. Neural networks are trained with a data set (or "dataset") to minimize a cost function, which is a measure of the neural network's performance. Training algorithms include, but are not limited to, backpropagation (BP). The training algorithm tunes the node weights and/or bias to minimize the cost function. It should be understood that any algorithm that finds the minimum of the cost function can be used to for training a neural network.

A convolutional neural network (CNN) is a type of deep neural network that has been applied, for example, to image analysis applications. Unlike an artificial neural networks, each layer in a CNN has a plurality filters which are responsible for extracting features. CNNs can include different types of layers, e.g., convolutional, pooling, and fully-connected (also referred to herein as "dense") layers. A convolutional layer includes a set of filters and performs the bulk of the computations. A pooling layer is optionally inserted between convolutional layers to reduce the computational power and/or control overfitting (e.g., by downsampling). A fully-connected layer includes neurons, where each neuron is connected to all of the neurons in the previous layer. The layers are stacked similar to artificial neural networks. GCNNs are CNNs that have been adapted to work on structured datasets such as graphs and can extract features from graph-like structures (e.g., molecules). Example GCNNs are described in Duvenaud, D. et al., "Convolutional Networks on Graphs for Learning Molecular Fingerprints," In the Proceedings of Advances in Neural Information Processing Systems 28 (NIPS 2015), Montreal, Canada, Dec. 7-12, 2015: 2215-2223. GCNNs can be implemented using a computing device (e.g., computing device 200 in FIG. 2) and DEEPCHEM, which is a Python-based tool used for deep learning in drug discovery. It should be understood that DEEPCHEM is provided only as an example tool and that the GCNN can be implemented using other hardware and/or software.

The method can include receiving a first data set 102 (transfer data in FIG. 1A) including a plurality of molecules. The molecules in the first data set can be expressed in a computer-readable format. Optionally, the computer-readable format can be Simplified Molecular Input Line Entry System (SMILES) notation. SMILES notation is a line notation known in the art that uses ASCII strings. It should be understood that SMILES notation is provided only as an example and that other line notations can be used. Alternatively or additionally, this disclosure contemplates that the first data set can include an MDL molfile (.MOL file extension) or structure-data file (.SDF file extension). The method can also include training the GCNN to initialize one or more parameters of the GCNN using the first data set. This is shown by reference number 104 in FIG. 1A. This disclosure contemplates that the parameters of the GCNN can be the weights assigned to the filters of the GCNN, the number of layers inside the GCNN, the number of filters within each layer of the GCNN, the number of neurons at the fully connected layer, learning rate during training, and/or the number of instances (or samples) within each training batch. The parameters of the GCNN are initialized prior to training the GCNN using the training data. In other words, the GCNN is pretrained using the first data sets 102. The method can also include receiving a second data set 106 (training data in FIG. 1A) including a plurality of molecules. The molecules in the second data set can be expressed in a computer-readable format, for example, optionally SMILES notation. Additionally, the second data set can also include respective inhibition rates for a disease (e.g., malaria in Example 1 or cancer in Example 2 below) and the GCNN's goal is to predict the level of this inhibition rate from the second dataset 106, which includes the inhibition rates. For example, the inhibition rates come in play at the loss function error where the prediction of the GCNN is compared to the ground truth (inhibition rate). The backpropagation is done considering the error from the loss function. The method can also include training the GCNN to refine the one or more parameters of the GCNN using the second data set. This is shown by reference number 108 in FIG. 1A.

The molecules in the first data set can be unrelated to the molecules in the second data set. In other words, the molecules in the first data set do not need to have a correlation with molecules in the second data set. The main properties of a transfer dataset (such as first data set in FIG. 1A or training data in FIG. 1B) are its size and the patterns within it. If the transfer dataset has many molecules and these molecules are diverse, then the model can learn the patterns within those molecules and employ them later when discriminating between the training dataset (or second data set in FIG. 1A) molecules. For example, for antimalarial drug discovery applications, the molecules in the first data set are not related to *P. falciparum*, while the molecules in the second data set include potential candidates for inhibiting *P. falciparum*. The molecules in the first data set can instead include candidates for treating a different, unrelated disease such as cancer. In Example 1 below, the first and second data sets are publicly available data. The first data set (such as transfer data in FIG. 1A or training data in FIG. 1B) was obtained from the PubChem Bio Assay (PCBA) database, which includes activities of small molecules generated by high throughput screening. In particular, the molecules in the first data set had been screened to find an enzyme that is a target for cancer therapy. The second data set (or training data in FIG. 1A) was obtained from publicly available GlaxoSmithKline (GSK) compounds, which includes results for Dd2 inhibition, selectivity, and 3D7 inhibition. The transfer data, which had been screened for use as a cancer drug, therefore had no relation to the training data, which had been screened for use as an antimalarial drug.

The method can further include defining each of the molecules (e.g., molecules in the first or second data sets) by a plurality of selected features. The selected features can include a type of atom in a molecule, a degree of the atom, an implicit valence of the atom, hybridization of the atom, an aromatic property of the atom, a number of hydrogen atoms connected to the atom, or combinations thereof. Additionally, the selected features can further include chirality of the molecule. By including chirality, it is possible to convert the molecules into graphs without losing spatial information. It should be understood that some different molecules (e.g., enantiomers, diastereomers, etc.) can have the same SMILES notation but different spatial structures. This disclosure contemplates that DEEPCHEM (or other software tool) can be used to describe molecules by features of the atoms. When chirality is included as a selected features, the molecules can be described with thirty two of about seventy five features offered by DEEPCHEM. Following featurization, the method can further include converting the molecules defined by the selected features into a plurality of respective graphs associated with each of the molecules. This disclosure contemplates that DEEPCHEM (or other software tool) can be used to convert the molecules described by selected features into graphical form. Additionally, the step of training the GCNN to refine the one or more parameters of the GCNN (e.g., step 108 in FIG. 1A) can include training the GCNN using the respective graphs.

Alternatively, or additionally, the method can optionally further include optimizing a plurality of hyper-parameters of the GCNN. This is shown by reference number 110 in FIG. 1A. This disclosure contemplates that hyper-parameter optimization (e.g., step 110 in FIG. 1A) can be performed before transfer learning (e.g., step 104 in FIG. 1A) and GCNN training (e.g., step 108 in FIG. 1A). Hyper-parameters are GCNN parameters that control the learning process. The hyper-parameters can be optimized using a third data set 112 (validation data in FIG. 1A) including a plurality of molecules. Similar to the first and second data sets, the molecules in the third data set can be expressed in the computer-readable format, for example, optionally SMILES notation. Additionally, this disclosure contemplates that molecules in the third data set can be defined by selected features and converted to graphical format as described above. The hyper-parameters can include a number of convolution layers, a size of each convolution layer (e.g., the number of convolutional filters within each layer), a number of neurons in a dense layer, a dropout for each layer, a number of epochs, a learning rate, and/or a batch size. This disclosure contemplates that DEEPCHEM (or other software tool) can be used to optimize hyper-parameters of the GCNN.

Some of the hyper-parameters above define the architecture of the GCNN, e.g., the number of convolution layers, the size of each convolution layer, and the number of neurons in the dense layer. As described above, convolutional layers include sets of filters and perform the bulk of the computations. It should be understood that a GCNN can include multiple convolutional layers. In some implementations, the optimal number of convolutional layers is optionally 3 (see e.g., Table 1 in FIG. 7). In some implementations, the optimal convolutional layer size is optionally 64 convolutional filters (see e.g., Table 1 in FIG. 7, where there are 64 convolutional filters per convolutional layer). The dense layer (or fully-connected layer) includes a plurality of neurons, where each neuron is connected to all of the neurons in the previous layer of the GCNN. In some implementations, the optimal number of neurons in the dense layer is optionally 256 (see e.g., Table 1 in FIG. 7). A dropout for each layer of the GCNN is another hyper-parameter that can be optimized. Dropout is the number of layer outputs that are randomly ignored, which can prevent overfitting issues. In some implementations, the optimal dropout for each layer is optionally 0 neurons (see e.g., Table 1 in FIG. 7). The remaining hyper-parameters are related to GCNN training, e.g., a number of epochs, a learning rate, and/or a batch size. An epoch is one forward and one backward pass of the entire set of training data (e.g., the second data set 106 or training data in FIG. 1). In some implementations, the optimal number of epochs is optionally 2 (see e.g., Table 1 in FIG. 7). The learning rate controls how often the neuron (or node) weights are adjusted during training. In some implementations, the optimal learning rate is optionally 0.0001 (see e.g., Table 1 in FIG. 7). The batch size in the number of samples per forward and backward pass of training data (e.g., the second data set 106 or training data in FIG. 1). In some implementations, the optimal batch size is optionally 128 (see e.g., Table 1 in FIG. 7). It should be understood that the hyper-parameters and/or the values for the same are provided only as examples. This disclosure contemplates that the GCNN can be characterized by different hyper-parameters and/or values for the same.

The step of optimizing a plurality of hyper-parameters of the GCNN (e.g., step 110 in FIG. 1A) can include setting a respective value for each of the hyper-parameters. Thereafter, the GCNN can be trained using a set of molecules from the second data set, and then the GCNN can be tested using the third data set. The steps of training and testing can be repeated for different respective values for each of the hyper-parameters. A set of respective values for each of the hyper-parameters can be selected to optimize performance of the GCNN. Hyper-parameter optimization can be performed using a grid search algorithm. Grid search algorithm, which can include trying different sets of hyper-parameters and choosing the best one, is a known approach in the art for hyper-parameter optimization and is therefore not described in further detail below. After performing hyper-parameter optimization (e.g., step 110 in FIG. 1A), transfer learning (e.g., step 104 in FIG. 1A) and GCNN training (e.g., step 108 in FIG. 1A) can be performed.

In some implementations, the third data set is lab-validated data. Lab-validated data for antimalarial drug discovery tends to be highly imbalanced. For example, in some cases, the hit rate can be around 2%, i.e., only two percent of lab tested molecules show activity. It should be understood that active molecules are the most important part of the data set since the GCNN is being trained to identify such active molecules. Thus, in order to provide a fair validation data set (e.g., the third data set 112 or validation data in FIG. 1A), the method can further include augmenting the validation data set to include additional copies of active molecules. This is shown by reference number 114 in FIG. 1A. This can be accomplished by copying active molecules in the validation data set to achieve a better balance between active and inactive molecules. In some implementations, a balanced validation data set includes about 50% active molecules and 50% inactive molecules. Optionally, a balanced validation data set includes about 40% active molecules and 60% inactive molecules. Optionally, a balanced validation data set includes between 40% and 50% active molecules (e.g., 40.0%, 40.1%, 40.2%, . . . 49.8%, 49.9%, 50%) and between 60% and 50% inactive molecules (e.g., 60.0%, 59.9%, 59.8%, . . . 50.2%, 50.1%, 50.0%) and any value or range therebetween. The optimal ratio between active and inactive molecules depends on the validation data itself. If validation data is diverse, the rule of thumb is to balance the dataset to include about 50% active molecules and 50% inactive molecules. If validation data is not diverse, sampling more will not help and balance the dataset to include about 40% active molecules and 60% inactive molecules or less may provide sufficient balancing, since creating more of the same data will not be useful. It should be understood that the above ratio of active molecules and inactive molecules is provided only as an example and that other ratios are possible. This disclosure contemplates that DEEPCHEM (or other software tool) can be used to augment the validation data set (e.g., the third data set 112 or validation data in FIG. 1A).

An example method for virtually screening molecules on *Plasmodium falciparum* (*P. falciparum*) is also described herein. *P. falciparum* is the parasite that causes malaria. The method can include providing a graph convolutional neural network (GCNN). This disclosure contemplates that the GCNN can be the trained GCNN in FIG. 1A, for example. Optionally, in some implementations, the GCNN can have an architecture defined by some of the hyper-parameters shown in Table 1 in FIG. 7. For example, the GCNN can include three convolution layers. Optionally, a size of each convolution layer is 64 convolutional filters. Alternatively or additionally, the GCNN can further include a dense layer (or fully-connected layer). Optionally, the dense layer includes 256 neurons.

The method can further include receiving a molecule, and predicting, using the GCNN, whether the molecule inhibits *P. falciparum*. The GCNN output is therefore a prediction of whether the molecule inhibits *P. falciparum*. The molecule can be expressed in a computer-readable format, e.g., optionally SMILES notation. Additionally, the method can further include classifying the molecule as an active molecule or an inactive molecule. This disclosure contemplates that an active molecule is a drug candidate for treating malaria.

Alternatively or additionally, the method can further include defining the molecule by a plurality of selected features, converting the molecule defined by the selected features into a graph, and inputting the graph into the GCNN to predict whether the molecule inhibits *P. falciparum*. The selected features can include a type of atom in the molecule, a degree of the atom, an implicit valence of the atom, hybridization of the atom, an aromatic property of the atom, a number of hydrogen atoms connected to the atom, or combinations thereof. Additionally, the selected features can further include chirality of the molecule.

Optionally, the method can further include confirming active molecules identified using the GCNN as drug candidates for treating *P. falciparum* using an in-vitro test.

Figure 1B:
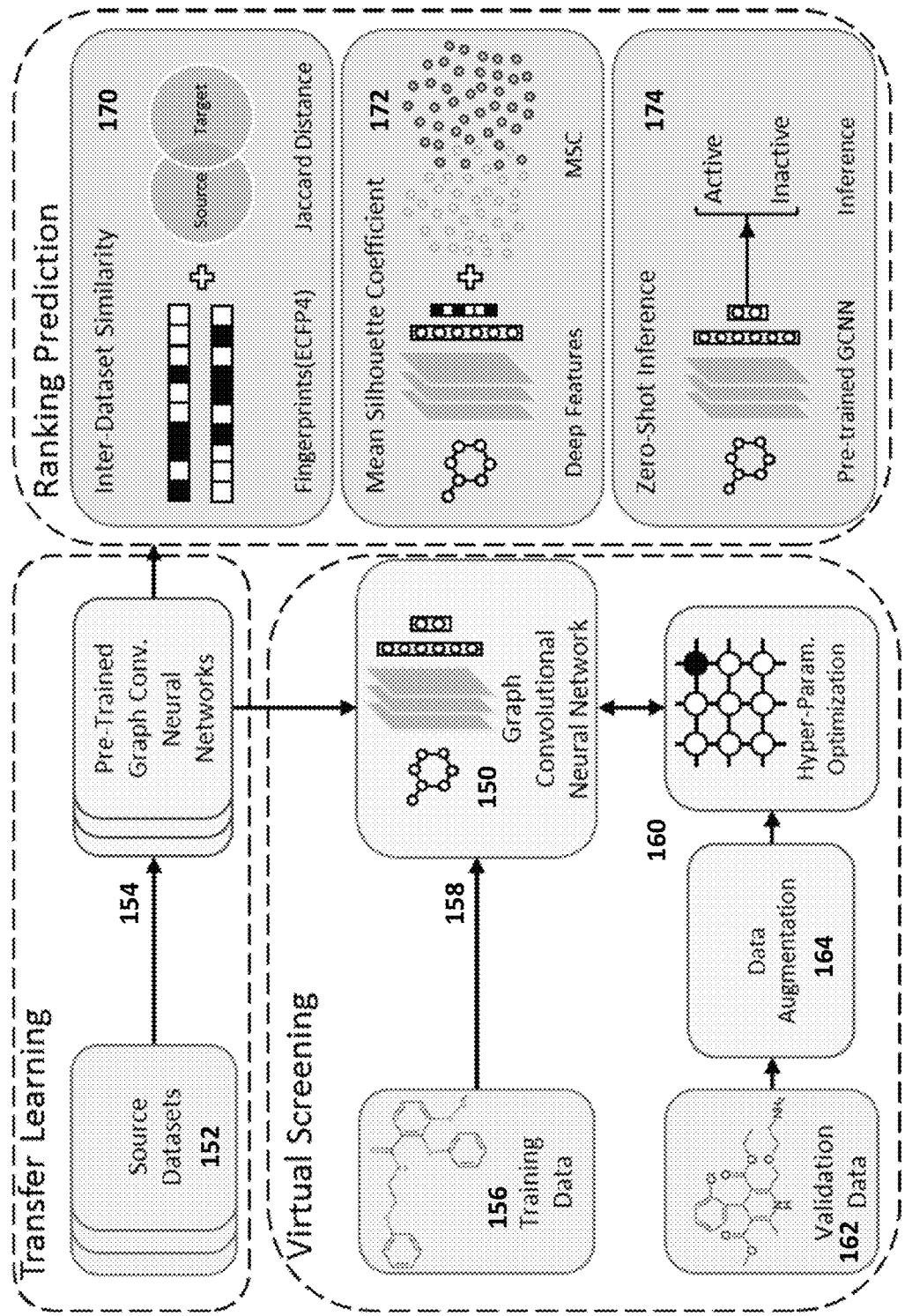
FIG. 1B is a diagram illustrating example operations for training a graph convolutional neural network (GCNN) configured for virtual screening of molecules for drug discovery according to another implementation described herein.

Referring now to FIG. 1B, another example method for training a graph convolutional neural network (GCNN) 150 configured for virtual screening of molecules for drug discovery is described. In FIG. 1B, the GCNN is configured for anti-cancer drug discovery. It should be understood that discovery of anti-cancer compounds is only provided as an example. This disclosure contemplates that the GCNN training method described herein may be used for other drug discovery applications. Similarly as described above with regard to FIG. 1A, the GCNN training method described below uses transfer learning to increase the accuracy of the GCNN. For example, transfer learning allows better initialization of the models and alleviates the problems caused from over-parameterization and imbalanced datasets. Additionally, the GCNN training method described below uses transfer learning to pretrain a plurality models, each trained using an independent data set. The learned knowledge is then transferred to the target task for fine-tuning, e.g., predicting p53-based bioactivity, which is an important factor for anti-cancer models. Optionally, the plurality of pretrained models can be compared and ranked such that the best model can be chosen for the target task fine-tuning.

The method can include receiving a plurality of source data sets 152 (source datasets in FIG. 1B), each source data set 152 including a plurality of molecules. The molecules can be expressed in a computer-readable format, for example, optionally SMILES notation. The source data sets 152 may be different and/or independent from each other. The source data sets 152 may have at least one of different data sizes, different data diversity, or different biological origin. For example, the source data sets 152 can be selected from a database such as MoleculeNet (see Example 2), which is a large-scale molecular database designed to enable machine learning model creation for molecular tasks. In Example 2 below, the source data sets originate from six different datasets.

The method can also include training a plurality of GCNNs to initialize one or more parameters of each of the GCNNs. This is shown by reference number 154 in FIG. 1B. GCNNs are described above in detail with regard to FIG. 1A. In addition, example GCNN parameters are described above in detail with regard to FIG. 1A. Each of the GCNNs can be trained using a respective one of the source data sets 152. For example, 182 different GCNNs are trained using 182 different source data sets in Example 2. It should be understood that the number of GCNNs and/or source data sets provided above are only examples. This disclosure contemplates training a different number of GCNNs than provided in the examples. Optionally, a GCNN is trained using a source data set for more epochs than the GCNN is trained using a training data set. For example, a GCNN can be trained using a source data set for 30 epochs while the GCNN can be trained using a training data set for 1 epoch (see Example 2). It should be understood that the number of epochs provided above are only examples. This disclosure contemplates training the GCNN for more or less epochs than provided in the examples. As described above, the respective parameters of each of the GCNNs are initialized prior to training the GCNNs using the training data. In other words, the GCNNs are pretrained using the source data sets 152.

The method can also include receiving a training data set 156 (training data in FIG. 1B) including a plurality of molecules. The molecules in the second data set can be expressed in a computer-readable format, for example, optionally SMILES notation. Additionally, the training data set 156 can include respective inhibition rates for a disease (e.g., malaria in Example 1 and cancer in Example 2) and the GCNN's goal is to predict the level of this inhibition rate from the training data set 156, which includes the inhibition rates. The method can also include training the GCNN to refine the one or more parameters of the GCNN using the training data set 156. This is shown by reference number 158 in FIG. 1B. Optionally, as described herein, the molecules in one or more of the source data sets 152 can be unrelated to the molecules in the training data set 156, which is used for fine-tuning the GCNNs.

Alternatively or additionally, the method can optionally further include optimizing a plurality of hyper-parameters of a GCNN. This is shown by reference number 160 in FIG. 1B. The step of optimizing a plurality of hyper-parameters of the GCNN (e.g., step 160 in FIG. 1B) can include setting a respective value for each of the hyper-parameters. A set of respective values for each of the hyper-parameters can be selected to optimize performance of the GCNN. Hyper-parameter optimization can be performed using a grid search algorithm as described above with regard to FIG. 1A. Optionally, in some implementations, this disclosure contemplates that hyper-parameter optimization (e.g., step 160 in FIG. 1B) can be performed before transfer learning (e.g., step 154 in FIG. 1B) and GCNN training (e.g., step 158 in FIG. 1B). Hyper-parameters are GCNN parameters that control the learning process. The hyper-parameters can be optimized using a validation data set 162 (validation data in FIG. 1B) including a plurality of molecules. The molecules in the validation data set 162 can be expressed in the computer-readable format, for example, optionally SMILES notation. The hyper-parameters can include a number of convolution layers, a size of each convolution layer (e.g., the number of convolutional filters within each layer), a number of neurons in a dense layer, a dropout for each layer, a number of epochs, a learning rate, and/or a batch size. This disclosure contemplates that DEEPCHEM (or other software tool) can be used to optimize hyper-parameters of the GCNN.

As described herein, the validation data set 162 may be highly imbalanced. For example, the hit rate in the validation data set 162 may include only a small percentage of molecules showing p53-based bioactivity (i.e., potential anticancer drug). It should be understood that active molecules are the most important part of the data set since the GCNN is being trained to identify such active molecules. Thus, in order to provide a fair validation data set, the method can further include augmenting the validation data set 162 to include additional copies of active molecules. This is shown by reference number 164 in FIG. 1B. This can be accomplished by copying active molecules in the validation data set 162 to achieve a better balance between active and inactive molecules. This disclosure contemplates that DEEPCHEM (or other software tool) can be used to augment the validation data set 162.

Example hyper-parameters, which define the architecture of the GCNN, are described above in detail with regard to FIG. 1A. In some implementations, the optimal number of convolutional layers is optionally 3 (see e.g., Table 10 in FIG. 30). In some implementations, the optimal convolutional layer size is optionally 64 convolutional filters (see e.g., Table 10 in FIG. 30, where there are 64 convolutional filters per convolutional layer). The dense layer (or fully-connected layer) includes a plurality of neurons, where each neuron is connected to all of the neurons in the previous layer of the GCNN. In some implementations, the optimal number of neurons in the dense layer is optionally 256 (see e.g., Table 10 in FIG. 30). A dropout for each layer of the GCNN is another hyper-parameter that can be optimized. Dropout is the number of layer outputs that are randomly ignored, which can prevent overfitting issues. In some implementations, the optimal dropout for each layer is optionally 0 neurons (see e.g., Table 10 in FIG. 30). The remaining hyper-parameters are related to GCNN training, e.g., a number of epochs, a learning rate, and/or a batch size. An epoch is one forward and one backward pass of the entire set of training data (e.g., the second data set 156 or training data in FIG. 1B). In some implementations, the optimal number of epochs is optionally 2 (see e.g., Table 1 in FIG. 7). The learning rate controls how often the neuron (or node) weights are adjusted during training. In some implementations, the optimal learning rate is optionally 0.0001 (see e.g., Table 10 in FIG. 30). The batch size in the number of samples per forward and backward pass of training data (e.g., the second data set 156 or training data in FIG. 1B). In some implementations, the optimal batch size is optionally 128 (see e.g., Table 10 in FIG. 30). It should be understood that the hyperparameters and/or the values for the same are provided only as examples. This disclosure contemplates that the GCNN can be characterized by different hyperparameters and/or values.

Alternatively or additionally, the method can optionally further include ranking each of the GCNNs trained using a respective one of the source data sets based on its respective predicted performance on the training data set. In some implementations, this may include analyzing a respective inter-dataset similarity between each of the source data sets 152 and the training data set 154 (see Example 2). This is shown by reference number 170 in FIG. 1B. The objective to find similarity between source and target data sets. If a pretrained GCNN (trained at reference number 154 in FIG. 1B) has seen similar data during training on source data, then the GCNN may have learned useful representations for the target task (e.g., predicting anti-cancer drugs). In some implementations, ranking models may include analyzing a respective ability of each of the GCNNs trained using a respective one of the source data sets 152 to distinguish between active and inactive target molecules (see Example 2). This is shown by reference number 172 in FIG. 1B. The objective is to find one or more pretrained GCNNs (trained at reference number 154 in FIG. 1B) that discriminate based on activity of the target molecules. The inner representations of such GCNNs may be easier to fine-tune and therefore may perform better for the target task (e.g., predicting anti-cancer drugs). Mean Silhouette Coefficient (MSC) calculations are an example metric. In some implementations, ranking models may include testing each of the GCNNs trained using a respective one of the source data sets 152 using a validation data set 162 (see Example 2). This is shown by reference number 174 in FIG. 1B. The objective is to find one or more pretrained GCNNs (trained at reference number 154 in FIG. 1B) that classify the validation data set 162 without fine-tuning. Such GCNNs may have been trained with source data similar to target data and/or discriminate based on activity of the target molecules. The inner representations of such GCNNs may be easier to fine-tune and therefore may perform better for the target task (e.g., predicting anti-cancer drugs).

It should be appreciated that the logical operations described herein with respect to the various figures may be implemented (1) as a sequence of computer implemented acts or program modules (i.e., software) running on a computing device (e.g., the computing device described in FIG. 2), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 2:
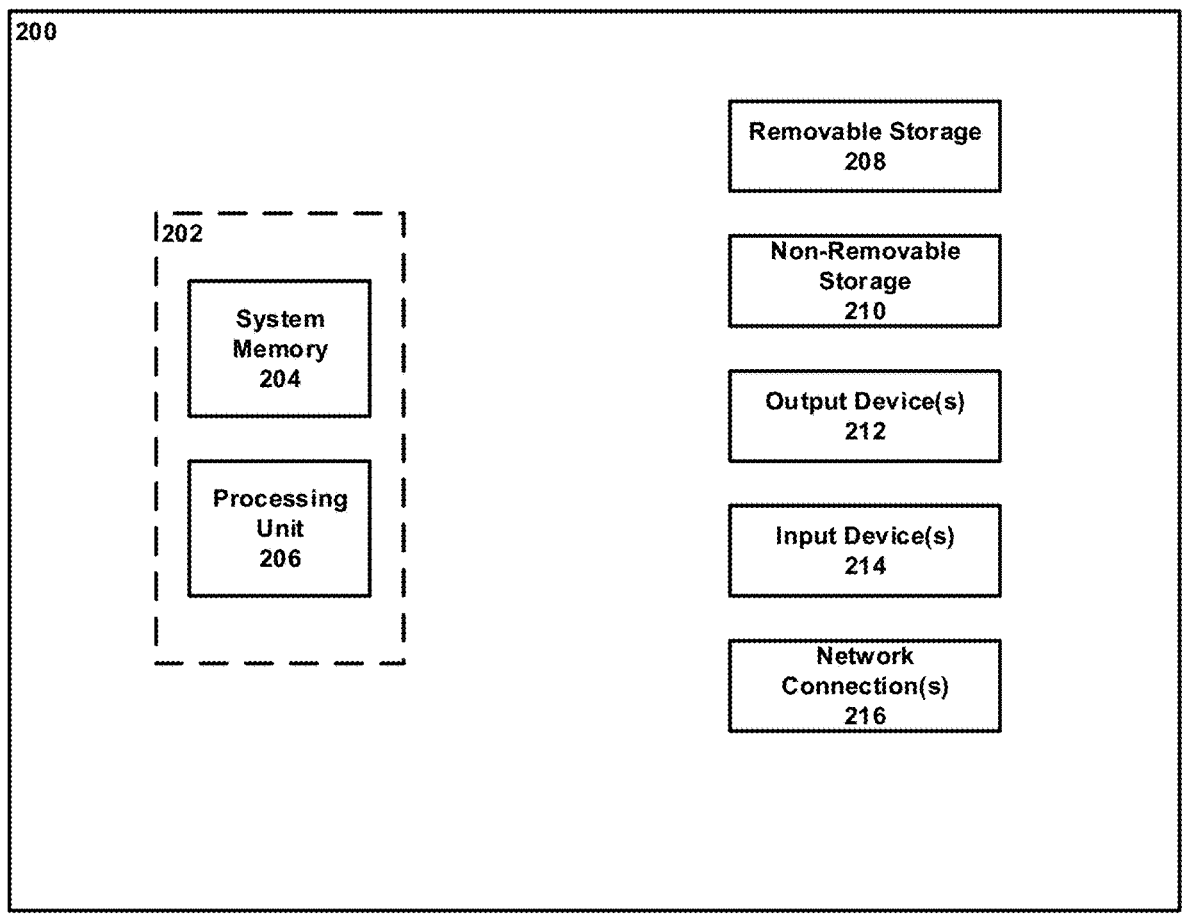
FIG. 2 is an example computing device.

Referring to FIG. 2, an example computing device 200 upon which the methods described herein may be implemented is illustrated. It should be understood that the example computing device 200 is only one example of a suitable computing environment upon which the methods described herein may be implemented. Optionally, the computing device 200 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 200 typically includes at least one processing unit 206 and system memory 204. Depending on the exact configuration and type of computing device, system memory 204 may be volatile (such as random access memory (RAM)), non-volatile (such as read-only memory (ROM), flash memory, etc.), or some combination of the two. This most basic configuration is illustrated in FIG. 2 by dashed line 202. The processing unit 206 may be a standard programmable processor that performs arithmetic and logic operations necessary for operation of the computing device 200. The computing device 200 may also include a bus or other communication mechanism for communicating information among various components of the computing device 200.

Computing device 200 may have additional features/functionality. For example, computing device 200 may include additional storage such as removable storage 208 and non-removable storage 210 including, but not limited to, magnetic or optical disks or tapes. Computing device 200 may also contain network connection(s) 216 that allow the device to communicate with other devices. Computing device 200 may also have input device(s) 214 such as a keyboard, mouse, touch screen, etc. Output device(s) 212 such as a display, speakers, printer, etc. may also be included. The additional devices may be connected to the bus in order to facilitate communication of data among the components of the computing device 200. All these devices are well known in the art and need not be discussed at length here.

The processing unit 206 may be configured to execute program code encoded in tangible, computer-readable media. Tangible, computer-readable media refers to any media that is capable of providing data that causes the computing device 200 (i.e., a machine) to operate in a particular fashion. Various computer-readable media may be utilized to provide instructions to the processing unit 206 for execution. Example tangible, computer-readable media may include, but is not limited to, volatile media, non-volatile media, removable media and non-removable media implemented in any method or technology for storage of information such as computer readable instructions, data structures, program modules or other data. System memory 204, removable storage 208, and non-removable storage 210 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 206 may execute program code stored in the system memory 204. For example, the bus may carry data to the system memory 204, from which the processing unit 206 receives and executes instructions. The data received by the system memory 204 may optionally be stored on the removable storage 208 or the non-removable storage 210 before or after execution by the processing unit 206.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

EXAMPLES

Example 1

DeepMalaria

Resistance has emerged for all current antimalarials including the frontline treatment Artemisinin, facilitating the need for new drug candidates with alternative targets. The traditional approaches to High Throughput Screening (HTS) for hit identification are often time-consuming and expensive. While virtual screening allowing for the identification of drug candidates in-silico might alleviate this problem, the available models often suffer from limited generalization. Meanwhile, Artificial Intelligence (AI) models have demonstrated the potential for highly accurate performance in the field of chemical property prediction using either structural-based or ligand-based approaches. Leveraging this ability along with the existing datasets, AI based systems could be a suitable alternative to HTS or fingerprint-based virtual screening. A deep learning model would allow for the incorporation of abstract patterns from existing data to aid in the search for hit compounds. In this example, DeepMalaria, a deep learning-based process capable of predicting the activity of compounds against *Plasmodium falciparum* while also predicting the relative cytotoxicity in human cell line HepG2, is introduced. The graph-based model was trained on 13,446 publicly available GlaxoSmithKline (GSK) compounds and was used to identify drug candidates from a test dataset. The in-silico pipeline for this process consists of external validation on an in-house independent dataset consisting mostly of natural product compounds. Transfer learning from a large dataset was leveraged to improve the performance of the deep learning model. Compound activity was then confirmed against *P. falciparum* in a phenotypic SYBR Green I based assay in-vitro. DeepMalaria correctly identified 87.75% of compounds with an inhibition rate of 50% or more in a test dataset. Moreover, the model was able to recall 72.32% of the active molecules within the validation dataset. These results highlight the generalization capacity of DeepMalaria and the potential of deep learning techniques in discovering new drug candidates in-silico, alleviating some of the time and cost associated with early-stage antimalarial drug discovery.

In order to overcome the low hit rate of HTS, screened compounds need to be selected in an intelligent manner. If compounds libraries that are more prone to be bioactive are selected, the possibility of yielding a higher hit rate increase. This bioactivity can be predicted in-silico, in a process called virtual screening (Shoichet 2004). In this approach, models are created to predict the activity of a compound based on chemical properties of the compounds. One of the most common descriptors used for virtual screening is currently Extended Connectivity Fingerprint (ECFP) (Rogers and Hahn 2010). This descriptor uses the different existing sections of molecule to describe it. The most prevalent use of ECFP in Quantitative Structure—Activity Relationship (QSAR) models involves creating a fingerprint and using a neural network to perform prediction (Gupta, Gupta, and Rawal 2016; Ramsundar et al. 2015). This approach isolates feature extraction and decision making, not allowing the decision-making process to have an effect on the creation of fingerprints.

Since the last decade, Artificial Intelligence (AI) has shown encouraging results toward different fields of healthcare (Reddy, Fox, and Purohit 2019; Jiang et al. 2017; Wainberg et al. 2018; Zhavoronkov et al. 2019; Pérez-Sianes, Pérez-Sánchez, and Díaz 2016; Ching et al. 2018). One important area would be different types of drug discovery affected by AI such as Ligand-based VS (Mayr et al. 2016; Chen et al. 2018), target prediction (Mayr et al. 2018), Structural-based VS (Wallach et al. 2015), de novo molecular design (Guimaraes et al. 2017; Kadurin et al. 2017), or metabolomics approaches (Pirhaji et al. 2016). Deep learning approaches enable end-to-end classification of data via learning feature representation and decision making simultaneously. Deep learning's automatic feature extraction has shown superiority to traditional isolated feature extraction and caused the popularity of these models in many fields such as image recognition (Huang et al. 2016), signal classification (Rajpurkar et al. 2017), and Natural Language Processing (Devlin et al. 2018).

Recently, Graph Convolutional Neural Networks (GCNN) have shown high accuracy in predicting chemical properties of compounds (Aspuru-Guzik et al. 2016). These models transform the compounds into graphs and learn higher-level abstract representations of the input solely based on the data. Graph convolutional neural networks combine ECFP's concept of creating fingerprints from substructures with deep learning's automatic feature extraction. Compared to ECFP, the GCNN's features are shorter (encoding only the relevant features), contain similarity information for different substructures, and facilitate more accurate predictions (Aspuru-Guzik et al. 2016; Kearnes et al. 2016; Liu et al. 2018).

In this example, GCNNs are leveraged to assist in the antimalarial drug discovery process. The representative abilities of GCNNs are used to implement a virtual screening pipeline. These models take compounds as input and predict the *P. falciparum* inhibition and HepG2 toxicity of the given compounds, aiding in the intelligent selection of scaffolds for HTS input. The hyper-parameters of the model are optimized using an external validation on an independent and imbalanced dataset. To overcome the trouble of low training data, transfer learning is used. The model is initialized with the weights transferred from a model trained on a large unrelated dataset. The compounds are tested in-vitro in order to evaluate the model.

The contributions of this work include, but are not limited to, using GCNNs for non-targeted ligand-based virtual screening in antimalarial drug discovery, creating a practical pipeline for training generalizable virtual screening models, using deep learning techniques such as transfer learning and external validation to improve the model, and evaluating the results of the model in a prospective manner via comparison to in-vitro experiment results Materials and Methods
Overview This example consists of two main sections; in silico and in vitro. In silico, DeepMalaria enables virtual screening of molecules on *Plasmodium falciparum* using a deep learning model (e.g., the GCNN described with regard to FIG. 1A). At the core, the GCNN model acts as a classifier, predicting the inhibition of input molecules and classifying them as "active" or "inactive". In order to optimize the hyper-parameters of the deep learning model, the model is validated externally on an independent and augmented validation dataset. The optimized model is trained on the large transfer dataset to extract useful initialization weights from it. Then, the pre-trained GCNN model is trained on the training dataset. The overview of the method is shown in FIG. 1A.

Once trained, the model predicts the inhibition of the test data. In vitro, phenotypic screening was performed on the test library, and the in silico predictions and in vitro results are compared. Once the hits are identified, Stage Specific Assay (SSA) and rate of killing assay were performed for each hit to better understand their mechanism of action in the Pf.

Data
Training Data (Gamo et al. 2010) tested around two million molecules on *P. falciparum* and found thousands of possible leads that possessed a high inhibition. The lead molecules are published and are publicly available in the supplementary materials of the article (Gamo et al. 2010). This consists of about 13,446 molecules. DeepMalaria uses Dd2 (Pf line resistance to Chloroquine) inhibition and selectivity for training. The molecules are classified as one if they possess Dd2 inhibitions of 50% and higher and zero if otherwise. The developed resistance in *P. falciparum* has caused these molecules to affect 3D7 (Pf line sensitive to Chloroquine) and Dd2 strains differently, with most of the molecules in the GSK dataset possessing high 3D7 inhibition and varying Dd2 inhibition. Therefore, the training data implicitly holds information about the developed resistance, and if the model is trained on Dd2 inhibition data it would be able to predict if resistance has been developed or not.

Validation Data

The validation dataset consists of the results from previously performed HTS processes in the laboratory, consisting of natural-products, kinase inhibitors and ChemDiv libraries. This dataset contains 4,497 molecules and their inhibition percentage. Overall, this dataset possesses 112 molecules that have an inhibition higher than 50%. Via using this external validation dataset, the realistic capabilities of the model are evaluated in the validation process.

Source Data for Transfer Learning

In order to perform transfer learning, a large dataset is chosen as the source to transfer from. One of the largest labeled molecule datasets is publicly available in the PubChem Bio Assay (PCBA) repository. Within this dataset, the "PCBA-686979" assay (Wu et al. 2018; PubChem Database 2019) contains 303,167 molecules with 20.82% of them being active. The molecules in the mentioned library are not related to *Plasmodium*, and they were screened to find Inhibitors of human tyrosyl-DNA phosphodiesterase 1 (TDP1). This enzyme is a target for cancer therapy in spite of not being necessary protein for human cells. This unrelated large and high variance collection is chosen as the source for transfer learning solely based on its size.

In Silico
Graph Convolutional Neural Network Model

In this example, DeepChem's (Ramsundar et al. 2019) implementation of GCNN is used. This implementation offers the creation of architectures with graph convolutional layers, graph pooling layers, dropout layers, graph gather layers, and fully connected layers. The molecular graph is sorted via atom index in order to attain the same graph for canonical SMILES. The training data is first cleaned by removing the molecules with missing inhibition. Having done so, the molecules that are lengthy are removed since they might be harmful in the training process of the model. Two details need to be considered in the conversion of molecules to graphs; firstly, the nodes represent different atoms and need to contain information of this difference. In order to differentiate between the atom nodes, Deepchem offers 75 different features for describing each atom. In this example 29 of those features are used containing the type of atom, atom's degree, atom's implicit valence, atom's hybridization, atom's aromatic properties, and total number of Hydrogen connected to the atom. Secondly, in order to convert molecules to graph and not lose special information, chirality was added to the features.

Data Augmentation and Hyper-Parameter Optimization

The validation dataset for this work, i.e. the "lab dataset" is highly imbalanced. Only 2% of the molecules within the dataset show activity. These molecules are also the most important part of the dataset, since the goal of the model is to find active molecules. In order to have a fair validation on this dataset, the data needs to be balanced first. The data augmentation process created more copies of the active molecules after shuffling the atom orders. This balancing process is done via SMILES Enumeration (Bjerrum 2017), creating on average 38 copies of each active molecule.

The augmented validation dataset can be used for finding the optimum topology, hyper-parameters, and epochs for training. Starting with the topology, the hyper-parameters that can be defined are the number of convolution layers, the size of each convolution layer, number of neurons in the dense layer, and the dropout of each layer. The remaining hyper-parameters that can be defined are the learning rate and batch size. To perform hyper-parameter optimization and find a fitting architecture, grid search is performed. Different values are chosen for each hyper-parameter, the model is trained on the training dataset and tested on the validation dataset. The set of hyper-parameters that has the best performance is chosen, and the architecture and variables of the model are finalized.

Transfer Learning

Training a deep learning model often requires a large amount of data since the algorithms contain numerous variables that are optimized during training. DeepMalaria's training dataset is in the order of a few thousands, which compared to the image domain datasets is considered low amount of data. This low amount of data makes the training of the model to be sensitive to its initial weights. In order to overcome this challenge, transfer learning is used from a large source dataset. It has been shown that the source dataset does not necessarily need to have correlation with the target dataset. The patterns within the molecules of the transfer dataset (PCBA) can help initialize the GCNN and make the training on the target dataset (GSK) to be more efficient. After the optimized architecture for model is found, the model is trained on the source dataset for 50 epochs, then the weights are saved and restored in the beginning of training on the training dataset.

Transfer learning is new to the field of drug discovery. It has mainly been used in the form of multitask learning (Ramsundar et al. 2015) and related databases (Zhang et al. 2016) on artificial neural networks. This is different from the approach described herein in two ways; firstly DeepMalaria uses unrelated data, creating more opportunities and less constraint for implementing transfer learning and increasing the accuracy of any drug discovery model. Secondly, Deep-Malaria uses transfer learning on graph convolutional neural network rather than simple artificial neural networks, which is the first of its kind in drug discovery domain.

Evaluation of the Model

In order to assess the performance of the model, evaluation metrics are needed. One evaluation metric that is commonly used for classification task is accuracy. If the model can correctly classify active compounds as active (true positive or "TP") and inactive compounds as inactive (true negative or "TN"), it would have a high accuracy. If the model is missing the active molecules and is incorrectly classifying them as inactive (false negative or "FN"), or if the model is predicting inactive molecules to be active (false positive or "FP"), the accuracy would be decreased. Table 1 in FIG. 7 shows these categories for the results of classification.

With these definitions in mind, accuracy is defined as:

$$\text{Accuracy} = \frac{TP + TN}{TP + TN + FP + FN}$$

In the field of drug discovery, having a high TP and a low FN is highly important, since the purpose of the model is to predict the active molecules that are few in number. One metric that can represent the ability of the model to capture active molecules is recall, as defined below:

$$\text{Recall} = \frac{TP}{TP + FN}$$

Since the test dataset for antimalarial drug discovery is imbalanced (e.g., has a low hit rate), accuracy would be a misleading metric. An untrained model can classify every input as inactive and still have an accuracy of nearly 97%. Moreover, recall alone would not be enough to evaluate models in imbalanced setting, since it does not contain any information of the performance of the model on the inactive molecules. To fully display model's behavior, normalized confusion matrix is used to show the percentage of data classified as each classification category. Furthermore, the Area Under the Receiver operation Characteristic Curve (ROC-AUC or AUC) is used as a fair score metric.

In Vitro
Preliminary Screening and Half Maximal Concentration Determination

Automated one-point phenotypic screening performed against multi-drug resistant *P. falciparum* strain Dd2 (resistant to Chloroquine) using a SYBR Green I assay (Vossen et al. 2010). An EVO-150 robot (Tecan) was used to aliquot compounds with final concentration of 1 µM, and then culture was added to the 96 well plate by hand at 1% parasitemia, 2% hematocrit. Plates were incubated for 72 h at 37° C. in 5% CO2 prior to freezing. Plates were subsequently thawed and 1× SYBR Green I was added with lysis buffer (20 mM Tris-HCl, 0.08% saponin, 5 mM EDTA, 0.8% Triton X-100). After incubation at room temperature for one hour, the fluorescent emission was measured at 485 nm excitation and 530 nm emission using BioTek plate reader. Preliminary hits were then screened for EC50 determination with SYBR Green I. Each compound was added with nine different concentration starting at 5 µM, assayed using 1:2 dilution. Nontreated wells and the ones treated with Chloroquine at 1 µM served as control. Curve fitting was performed using GraphPad Prism and $EC_{50}$ acquired.

Cytotoxicity Screening on HepG2 Cell Line

Selectivity was determined by using human cell line HepG2 in a MTS (3-(4,5-Dimethylthiazol-2-yl)-5-(3-carboxymethoxyphenyl)-2-(4-sulfophenyl)-2H-tetrazolium) based cytotoxicity assay (Riss et al. 2004). Briefly, microtiter plates were seeded with 1,500 cells per well in a 384 well plate and incubated for 24 h at 37° C. in 5% CO2. The next day, compounds were added in seven different concentration starting at 25 µM (with 1:2 dilution) and then incubated for 48 h at stated conditions. MTS solution was then added to each well and incubated for three hours and absorbance was read at 490 nm using BioTek plate reader. Nontreated wells and the ones treated with Chloroquine at 1 µM served as control. Curve fitting was performed using GraphPad Prism and $EC_{50}$ acquired.

Stage-Specific Activity Assay

Dd2 cell line were synchronized using a combination of 5% sorbitol and magnetic column separation. Culture at 2% parasitemia 2% hematocrit was plated into microtiter plates and measurements began six hours post invasion (6 hpi). Hit compounds were added at 3× $EC_{50}$ concentration at specified time points. Controls are DHA (3× $EC_{50}$) and nontreated cultures. Giemsa slides were made from each time point and culture was fixed for flow cytometric reading using 0.25% glutaraldehyde. After fixing and aspirating, 25% Triton-100 was added prior to washing and then 0.05 mg/ml RNAse was added and incubated for 3 hours. After incubation, 1/2500 of YOYO 1 was added and samples were read using flowcytometry (CytoFlex).

Rate of Killing Determination

Dd2 was synchronized using the mentioned methods then plated into 24 well plates at 2% parasitemia and 2% hematocrit at 0 hpi. Compounds were added at 0, 18, or 30 hpi with a final concentration of 5× $EC_{50}$. Each well was exposed to compound for either 6 or 12 hours using DHA (5× $EC_{50}$: 25 µM) and nontreated wells as controls. The experiment was done for each asexual stage of Pf if the hits were active in the stage. After washing compounds, the media was changed two times a day. The parasitemia was tracked for six days after adding compounds. All slides were dyed using Giemsa, and parasitemia was counted using microscope.

Results

In Silico Training Results

Figure 3B:
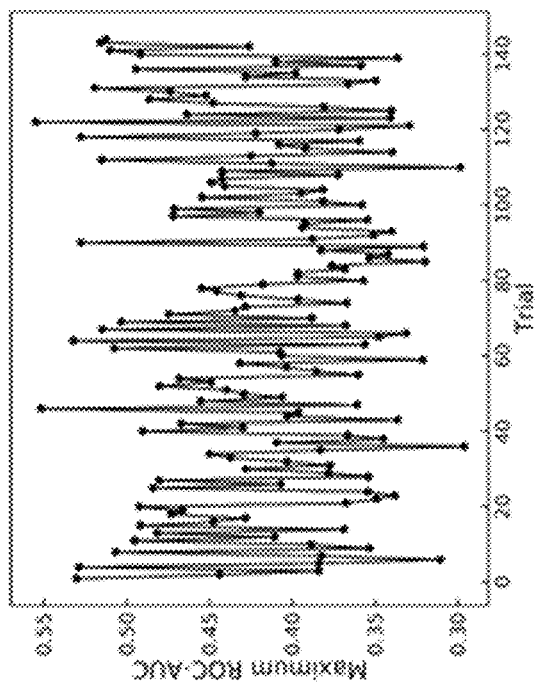
FIGS. 3A and 3B are graphs illustrating grid search results for different sets of hyper-parameters; average (FIG. 3A) and maximum (FIG. 3B).
Figure 3A:
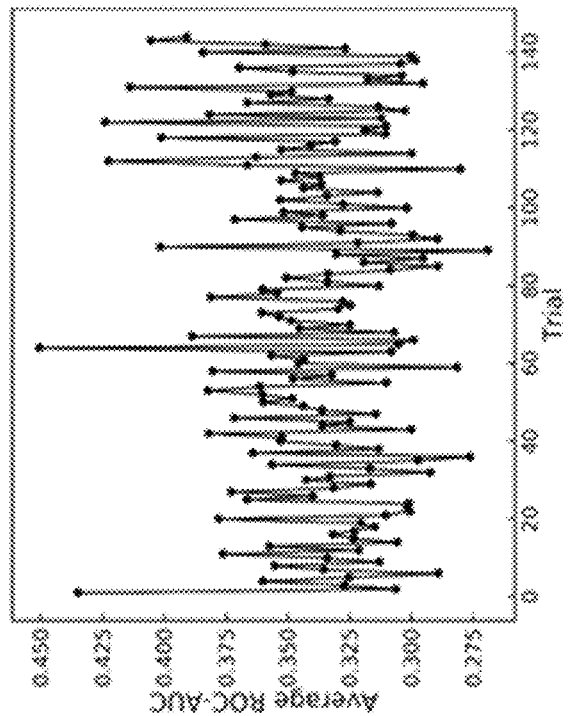

The results of the grid search for hyper-parameter optimization are shown in FIGS. 3A and 3B. Overall 144 different combinations of hyper-parameters were chosen for training and the trained model was tested on the validation dataset.

Trial 121 is among the hyper-parameters that yielded high average ROC-AUC scores, and it achieves the highest score between all trials. These hyper-parameters were chosen as the optimum variables and are shown in Table 2 in FIG. 8.

Having defined the architecture of the GCNN model, the model is trained on the transfer dataset. The weights are then saved and loaded for the main training process to start. At each epoch the AUC score on the training dataset and the validation dataset are calculated and recorded. The results are shown in FIG. 4.

Figure 4:
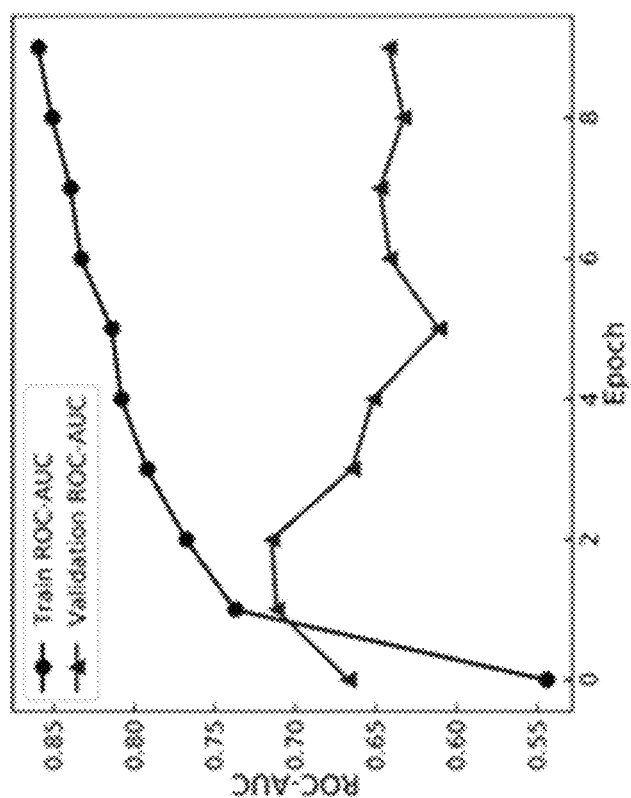
FIG. 4 is a graph illustrating Area Under the Receiver operation Characteristic Curve (AUC) scores of the GCNN described herein (DeepMalaria, Example 1) during training.

As it is visible from FIG. 4, the model starts to perform differently on the validation dataset from the training dataset after the $2^{nd}$ epoch. While the score on the training dataset rises and model learns the training dataset more, the performance on the validation dataset drops. These results demonstrate over fitting happening after the $2^{nd}$ epoch. Therefore, the model from this epoch is loaded as the trained model and the optimum duration of training is found.

Phenotypic Screening and Cytotoxicity Assessment

Evaluation of the model was performed by testing compounds phenotypically. To decrease validation bias in this experiment, the in-silico results were not considered when buying the library, and all compounds were purchased based on their drugability as identified using traditional cluster analysis (data not shown). To evaluate the results of the model predictions in-vitro in a method independent from in-silico results, all compounds were screened phenotypically. Multi-drug resistant Dd2 strain was used to provide clinically relevant results. Of the 2,400 compounds in the test dataset, 48 showed inhibition of parasitemia at greater than 50% at 1 µM. This is a comparatively high hit rate (~2%).

In Vitro and In Silico Results Comparison

After phenotypic screening in vitro, the ground truth labels for the test dataset are found. The model can now be evaluated both retrospectively and prospectively, via its prediction on the validation dataset and the test dataset. The results of this evaluation are shown in Table 3 in FIG. 9.

The model yields a high recall in both the validation and the test dataset, showing the ability of the model in finding active compounds. To fully display the performance of the model, the confusion matrices of the validation and test dataset are shown in FIGS. 5A and 5B.

Figure 5B:
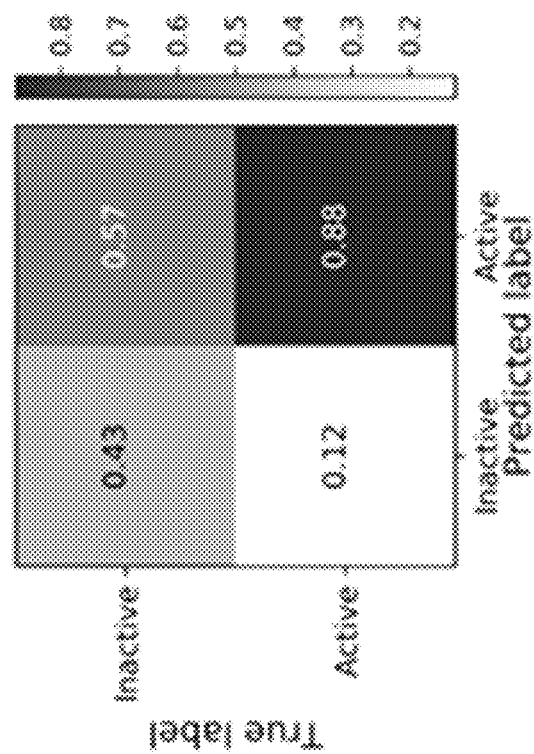
FIGS. 5A and 5B are confusion matrices of validation dataset (FIG. 5A) and test dataset (FIG. 5B).
Figure 5A:
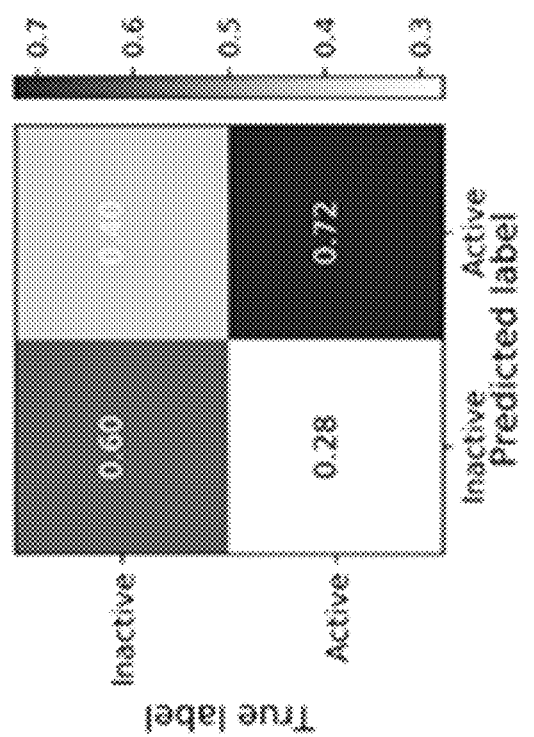

FIGS. 5A and 5B show similar behavior of the model on active molecules in the validation dataset and the test dataset, achieving the goal of the external validation process in DeepMalaria. Moreover, the model is inclined to predict the input as active, yielding a higher false positive rate than false negative rate. This behavior is essential to a drug discovery model, since finding the active molecules are of priority, and falsely predicting them as inactive is detrimental to the process.

Figure 6:
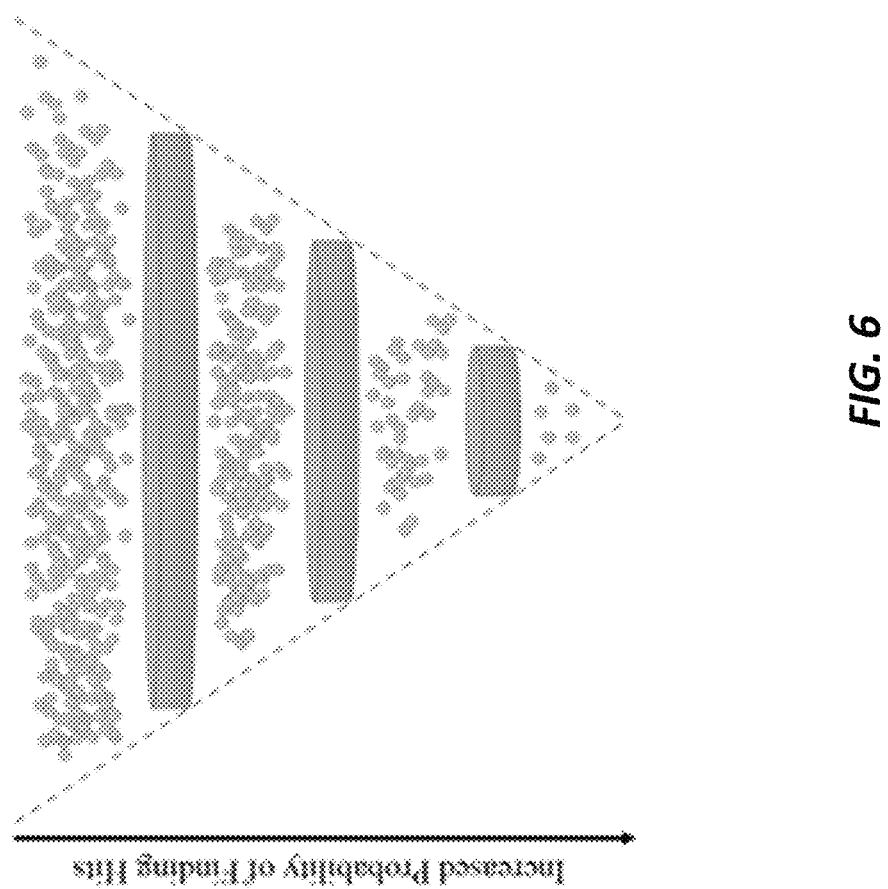
FIG. 6 illustrates how the GCNN described herein (DeepMalaria, Example 1) finds potent hits with higher recall. 87.85% for hits with inhibition of 50% or more, 100% for nanomolar active hits.

Furthermore, the model was able to correctly predict all of the 6 compounds with Nano-molar activity. To determine the confidence of the model in the prediction, the output value of the softmax layer is recorded and presented. In order to predict the toxicity of the compounds, the model was trained with the same parameters used for inhibition, however, the training data is changed to contain toxicity information. In early drug discovery, scientists mostly try to find compounds with nanomolar activity, and other hits will not enter further phases of drug development. Recalling 100% of the nanomolar active hits proves the potential of Artificial Intelligence as a fast and low-cost technique in early stage drug discovery (FIG. 6).

Comparison to Other Methods

The external validation process can also be used for traditional approaches of virtual screening. As in traditional approached, a Random Forest (RF) model is trained on the ECFP of the molecules after optimized hyper-parameters were found. Furthermore, in order to evaluate the impact of transfer learning, a model (GCNN) without transferred weights is trained. The results are shown in Table 4 in FIG. 10.

The RF model predicts most of the input molecules as active, resulting in an impractical model. The GCNN in DeepMalaria can outperform RF without transfer learning, showing the superiority of learnt features during training (in GCNN) to isolated feature extraction (ECFP). Additionally, by adding transfer learning, the model gains a noticeable boost in performance, correctly predicting more active and inactive molecules. This shows the potential of DeepMalaria's process in early hit prediction.

Conclusion

In this example a deep learning model was trained on publicly available data to predict *Plasmodium falciparum* inhibition of compounds. A validation dataset was created from previous experiments and was augmented to assist in hyper-parameter optimization. Transfer learning from a large corpus of unrelated data was employed to facilitate the training of the deep learning model. The model was tested on an independent test dataset in order to find new drug candidates. DeepMalaria was able to find 72.32% of active molecules from the validation dataset and 87.75% of that of the test dataset, while maintaining an acceptable accuracy in an imbalanced setting. The results show that deep learning automatic feature extraction can learn patterns within the molecules that are generalizable to new and unseen datasets, outperforming the traditional approach of classifying fingerprints. DeepMalaria has shown increasing accuracy when predicting more potent compounds, a very important characteristic which do not let any nanomolar active/nontoxic compound to be missed. Furthermore, the hit compounds were narrowed down to one fast-acting compounds working in all stages of *P. falciparum*.

Example 2

TranScreen

Deep learning's automatic feature extraction has proven its superior performance over traditional fingerprint-based features in the implementation of virtual screening models. However, these models face multiple challenges in the field of early drug discovery, such as over-training and generalization to unseen data, due to the inherently unbalanced and small datasets. In this example, the TranScreen pipeline is described, which utilizes transfer learning and a collection of weight initializations to overcome these challenges. An amount of 182 graph convolutional neural networks are trained on molecular source datasets and the learned knowledge is transferred to the target task for fine-tuning. The target task of p53-based bioactivity prediction, an important factor for anti-cancer discovery, is chosen to showcase the capability of the pipeline. Having trained a collection of source models, three different approaches are implemented to compare and rank them for a given task before fine-tuning. The results show improvement in performance of the model in multiple cases, with the best model increasing the area under receiver operating curve ROC-AUC from 0.75 to 0.91 and the recall from 0.25 to 1. This improvement is vital for practical virtual screening via lowering the false negatives and demonstrates the potential of transfer learning. The code and pre-trained models are made accessible online.

Introduction

Drug development is a long and costly process during which a drug candidate is discovered and widely tested to be both efficient and safe. This process can take an average of 12 years with billions of dollars spent per drug [1,2]. The early stages of this process involve discovery of a drug candidate which is bio-active towards the targeted disease and is non-toxic for humans. Since High Throughput Screening (HTS) of big library of molecules for discovery of a potent scaffold is very inefficient, for decades, scientists have been working on modeling the bio-activity in silico and virtually screening the molecules. Since the screening takes place in simulation with no wet-lab effort, the cost and time of early drug discovery can be drastically decreased.

Traditionally, molecular descriptors and fingerprints are used to extract features from the input molecules, which are then passed to a machine learning model for training. This pipeline has been used for many virtual screening tasks such as kinase inhibition prediction [3], side-effect prediction [4], cytotoxicity prediction [5], and anti-cancer agent prediction [6]. In the recent years, deep learning models have proven to be capable, and in some cases superior [7], virtual screening tools for predicting the bio-activity of given molecules. The automatic feature extraction offered by deep learning models has been demonstrated to enable de novo drug design [8], Pharmacokinetics profile prediction [9], and bio-activity prediction [10]. Since the performance and accuracy of the screening models have a direct effect on the outcome of drug development pipelines [11], deep learning offers practical virtual screening. However, deep learning models are over-parameterized and data hungry models, thus face challenges in the virtual screening domain. These challenges are at heart of what this work examines and aims to address.

One of the main challenges of virtual screening is overfitting on the imbalanced and small training datasets [12]. In most molecular training datasets, the active molecules are rare and make up the minority distribution in the dataset, with inactive molecules outnumbering them heavily. Moreover, the number of total data points within available datasets is low due to the cost of screening in vitro. The significance of this challenge becomes palpable when a virtual screening model is trained on a non-diverse training dataset and tested on a large and diverse dataset. This scenario is often the case in many virtual screenings for drug discovery [13], and needs to be addressed for models to be practical in real-world applications.

A handful of solutions have been adapted to virtual screening from other domains of deep learning to battle this challenge. For virtual screening drug discovery, the problem of low and imbalanced data is handled traditionally using expert-made features [14], and in more recent years with a few applying multitask learning [15], few-shot learning [16], and unsupervised pre-training [17], with results showing performance improvement or deterioration in various cases. Transfer learning, which is the focus of this example, allows better initialization of the models and alleviates the problems caused from over-parameterization and imbalanced datasets. A wide-scale study of transfer learning, a collection of models to transfer from, and the study of models' behavior are lacking from the virtual screening domain.

In this example, transfer learning is applied for a virtual drug screening in a wide-scale manner. A p53-based dataset is chosen as the virtual screening task due to its importance for anticancer discovery, the imbalanced property of the dataset, and the fact that high sensitivity to weight initialization is observed in its baseline model. The results are compared to a related work, which uses reinforced multi-task learning to classify the same task [18]. The behaviors of the models are analyzed via ranking the model's predicting capability before its training on target data. The main contributions of this work are:

TranScreen pipeline: A practical pipeline is developed, which enables the usage of graph convolutional neural networks (GCNNs) for virtual screening and transferring the learned knowledge between multiple molecular datasets.

Creation of a collection of weights, which can be used as network initializations.

Comparing three methods of ranking models before fine-tuning takes place to select the model for future tasks.

Materials and Methods

Overview of the TranScreen Pipeline

The pipeline implemented in this example aims to apply transfer learning to a graph-based virtual screening model in a practical manner. The source datasets (from MoleculeNet) used for transfer learning and the target dataset (related to cancer) offer simple molecular-input line-entry system (SMILES) strings as input, and bio-activity or inhibition class as output to the models. The datasets are preprocessed and partitioned based on scaffold into training, validation, and test splits. As seen in FIG. 1B, one common network architecture and set of hyper-parameters are chosen. The source datasets are used to train multiple GCNN models with the common architecture in their related task. The pre-trained networks are then transferred to the target task and the models are fine-tuned. The models are ranked based on how well they perform on the target test dataset. Three different approaches are implemented which use the source data, the deep features of the target validation dataset, or zero-shot inference to predict the rank of the pre-trained models before fine-tuning.

Data

Source Data

MoleculeNet [19] is a large-scale molecular database designed to enable machine learning model creation for molecular tasks. This database offers a unique collection of multiple tasks and diverse molecules, which makes it an ideal choice for transfer learning. The source datasets used in the TranScreen pipeline are chosen from MoleculeNet datasets that have SMILES information. These source datasets originate from six different datasets, namely PCBA, MUV, HIV, BACE, Tox21, and SIDER, consisting of in total 182 tasks (assays) and 582,914 molecules. The datasets are not combined, yet each task is taken as an independent dataset, creating 182 different source datasets which can be used to train the same number of source models. We have provided detailed statistics for each dataset in Table 5, which is shown in FIG. 11. Detailed information about name of the tasks is provided with reference to FIGS. 11-32.

Target Data

The p53 gene is mutated in roughly 50-60% of all human cancers [20], making it an important target for the understanding and treatment of cell abnormality. As it is mentioned in Appendix A, it is not entirely clear what pathways would become involved after p53 mutation and loss of function. Therefore, not all molecular targets of the resultant cancers are known, and prediction of candidate drugs is not always feasible. Therefore, four p53-based datasets (PCBA-aid902/aid903/aid904/aid924) were identified in which high throughput screening assays were performed to discover potential anticancer compounds. Since the molecules need to be potent against a cell line with no p53 expression (complete loss of function), which is still mutated and cancerous, PCBA-aid904 [21] is chosen as the target dataset, which used a p53 null cell in a non-permissive temperature assay. By doing so, scaffolds selectively inhibiting cancer cells with loss of p53 functionality can be predicted. Since the target data is from PCBA dataset of the MoleculeNet, it is removed from the source data. The three other tasks, namely PCBA-902, PCBA-903, and PCBA-924, were also deleted due to the close relation they had with the target dataset. The information regarding the target dataset is presented in Table 6, which is shown in FIG. 12. Due to the low number of active compounds, this dataset is highly imbalanced and only 0.12% of the molecules show bio-activity.

Data Preprocessing and Partitioning

During preprocessing, SMILES with bio-activity data are read from each dataset. The input SMILES do not need to be canonical since the model will rearrange the input atoms in a preset order. Chirality information can be included in each input in order to distinguish between isomers. For each task, 80% of the compounds are selected as training samples, while the rest are partitioned as test and validation dataset. Dataset partitioning is done in regards to scaffolds of the molecules, which ensures that similar molecules are put in same data splits and increases the variation between training, test, and validation splits.

The validation set is aimed to be used to tune the process and to find the optimum model. If this validation set is chosen at random from a non-diverse dataset, the model may be prone to memorization of specific features that represent the homogenous training distribution. The random partitioning will decrease the trained model's ability to be applied to unseen test datasets. Therefore, dataset partitioning is implemented based on scaffolds of the molecules to improve generalization abilities of the learned representations and increase the practicality of the model in real-world scenarios.

Model Creation and Training

Graph Convolutional Neural Networks

Traditionally, virtual screening models take fingerprints of the molecules as input representation [14]. One of the most popular fingerprint creation techniques is Extended Connectivity Fingerprint [22], which encodes the existence of specific sub-structures of the molecule into a binary array. In recent years, this technique has been improved with the addition of GCNN models [10]. These deep learning models learn from the data to extract useful feature representations during training, while building on the same concepts of circular fingerprints.

GCNNs have been successfully applied to many tasks in drug discovery such as drug-target interaction prediction [23], physiochemical properties prediction [15], and chemical reaction prediction [24]. Part of this success is owed to the fact that molecules inherently resemble graphs, with nodes representing the atoms and edges representing the bonds between the atoms. In this example, the DeepChem [25] implementation of GCNNs with Tensorflow backend are used. This framework also handles the conversion of molecules to graphs with featurization of atom types, atom bonds, number of Hydrogens, and formal charge.

Common Network Architecture

One common model architecture and set of parameters need to be defined so that all models within the pipeline can be transferred to the target task. An architecture that has proven to perform well on the molecular dataset or task can be chosen as the common architecture. Alternatively, hyper-parameter optimization can be done using a grid search over various parameters and using the validation data to find a best-performing model. However, in many cases in virtual screening, the validation data is highly imbalanced and the effects of active molecules on the result of the grid search are diminished. Therefore, using data augmentation in the form of SMILES Enumeration [26] is suggested in order to make more copies of the active molecules and make the validation set balanced. Thus, more importance is put on finding active molecules when searching for optimum hyper-parameters. In this example an architecture that has proven to perform well on the PCBA dataset is used as the common architecture. This architecture is adapted from the [27] (see also DeepMalaria of Example 1) which implements the aforementioned data augmentation and hyper-parameter optimization. The details of the common architecture are given in Table 10, which is shown in FIG. 30.

Baseline Model and Internal Validation

After the data is preprocessed and the model is defined, training on the target task can begin. The training set from the target data is used to train the GCNN with random initialization for 30 epochs. Over-training was avoided using internal validation; the model is saved at each epoch during training and the performances of the model on the training set and the validation set are compared. In a healthy training period, the model's performance is improved over time on both sets. However, when over-training occurs, a decline in performance is observed on the validation set. The model from the last epoch before over-training, which is the second epoch, is taken as the baseline model.

Transfer Learning and Fine-Tuning

Machine learning has been successfully applied to many fields such as natural language processing [28], speech recognition [29], structured data [30], and arguably most predominantly to the image domain [31]. The current state of the solutions to low and imbalanced data in the image domain include the use of data augmentation [32], multitask learning [33], few-shot learning [32], and general transfer learning [34]. The training procedure of the deep learning models can be highly sensitive towards the weight initialization. Authors in [35] demonstrated that in most initializations there is a winning set of weights that become dominant during training. The stochastic gradient descent procedure will focus on this sub-structure of the network, making the rest of the network susceptible to be removed during pruning. This sheds a new light on how network initialization affects the training and performance of a deep learning model. Unfortunately, the situation is exacerbated when deep learning models are used as virtual screening models, since they are over-parameterized models that are data-hungry and are faced with imbalanced, non-diverse, or small datasets.

The state-of-the-art solution in dealing with the initialization challenge would be the use of transfer learning [34]. This process can include the transfer of weights from a pre-trained model on one domain (source) to a model on another domain (target). These weights represent what the source model has learned from the source data and the patterns used to extract features from the data. Transfer learning has shown to improve performance in many cases, but also hurt the performance in some [36]. Transfer learning in virtual screening has also been sparsely implemented in the forms of multitask learning [15] and unsupervised pre-training [17].

In this example, a separate GCNN model is trained for each source task, making a total of 182 source models. These tasks are of different data size, data diversity, and biological origin. Each model is trained for 30 epochs and the weights are saved and transferred to the target task. The models are then fine-tuned on the target training set for one epoch.

Model Rank Prediction Before Fine-Tuning

After the models are trained, fine-tuned, and evaluated they can be ranked based on how well they performed on the target test dataset. This disclosure contemplates predicting the ranking before fine-tuning on the target dataset is initiated. A rank prediction method can provide useful recommendations for future tasks and there would not be a need to apply large scale transfer learning from all 182 models. This question is a derivative of domain shift [37] and requires the comparison of the nature of datasets and models from the source and target domains. There are two main approaches in the literature for ranking pre-trained models, either via training an alternative model [38,39] or via statistical methods [36,40,41]. In this example two of the statistical methods are implemented and a third solution is offered in order to take a step forward in model rank prediction.

Inter-Dataset Similarity Comparison

The intuitive solution for model ranking prediction is to examine the source and target datasets and find the similarity between them [42]. If the model has seen similar data during training on the source dataset, it might have learned useful representations for the target task. This intuition can also be seen in traditional virtual screening models, which are based on the concept that molecules that share common substructures (e.g., fingerprints) and have similar bio-activity. In this example, this method is adopted from time-series domain in the form of Inter-Dataset Similarity (IDS) comparison [36] and is implemented using ECFP molecular fingerprints. The Jaccard (Tanimoto) Coefficient is used to find the pair-wise similarity between molecules from the source dataset and the molecules from the target dataset. The results are averaged over the maximum of 10,000 molecules, due to the large size of calculations. Higher Jaccard Index represents more similarity between the datasets.

Mean Silhouette Coefficient on Deep Features

The second solution for ranking prediction is to understand how well the models distinguish between active or inactive target molecules. If the model's inner representations are able to discriminate based on the activity of target molecules, it might be easier to fine-tune the model and thus perform better on the target task. In order to do so, the Mean Silhouette Coefficient (MSC) calculation is adopted from the time-series domain [41] as the ranking prediction metric. This metric is used to evaluate the efficiency of a clustering algorithm based on how distinguished the clusters are from each other. This metric is applied to features extracted from the second to last layer of the model, in order to judge how well these features distinguish between active and inactive molecules from the target validation dataset. Higher MSC represents better discrimination between the clusters.

Zero-Shot Inference

One final approach to ranking prediction is to simply let the pre-trained model classify the target validation data without any fine-tuning, i.e., zero-shot inference. The intuition behind this approach closely follows that of the last two approaches. First, if the source dataset is similar to that of the target dataset, the model might perform better after fine-tuning. This similarity was tested in regards to the molecules in IDS, but is applied to the bio-activity labels in zero-shot inference. Second, if the model has learned to distinguish between active and inactive molecules of the target dataset, it might have a better performance after fine-tuning. The main difference to MSC is that now the ROC-AUC of predictions on the target validation dataset is used as a metric. This difference forces the knowledge learned within the last layer of the model to also be incorporated into the ranking metric, which was absent from the MSC method.

Evaluation

Performance of the models was evaluated using three different evaluation metrics, including accuracy rate, recall, and area under the Receiver Operation Characteristic curve (ROC-AUC). While accuracy is easily interpretable, it is not a good metric for a highly imbalanced dataset. On the other hand, ROC-AUC can demonstrate how well the model performs on both the majority and minority data distributions. Furthermore, the Boltzman-Enhanced Discrimination of the Receiver Operating Characteristic (BEDROC) is used as a performance metric [43]. This metric is often used in the molecular domain where datasets are commonly class imbalanced. Recall is used since it reflects how well the model is able to predict active molecules, and misclassifying the few active molecules in the dataset is a costly mistake in the field of drug discovery. For reproducibility purposes, all 182 trained models are provided.

Having acquired the three metrics for ranking models before fine-tuning, they are ranked in three different manners and compared to the ground truth ranking attained from fine-tuning on the target test set. In order to evaluate the ranking prediction, similar to [44], the correlation between the metrics and the improvement in ROC-AUC after transfer learning is calculated. Moreover, the number of accurate predictions between the top 10 models is recorded. Lastly, similar to [41], the Mean Reciprocal Ranking (MRR) is calculated for the predicted ranks, averaging on the top 10 predictions.

Results
Baseline Model Results

The baseline model is trained on the target dataset for 30 epochs. The progress of the model is shown in FIG. 13.

Figure 13:
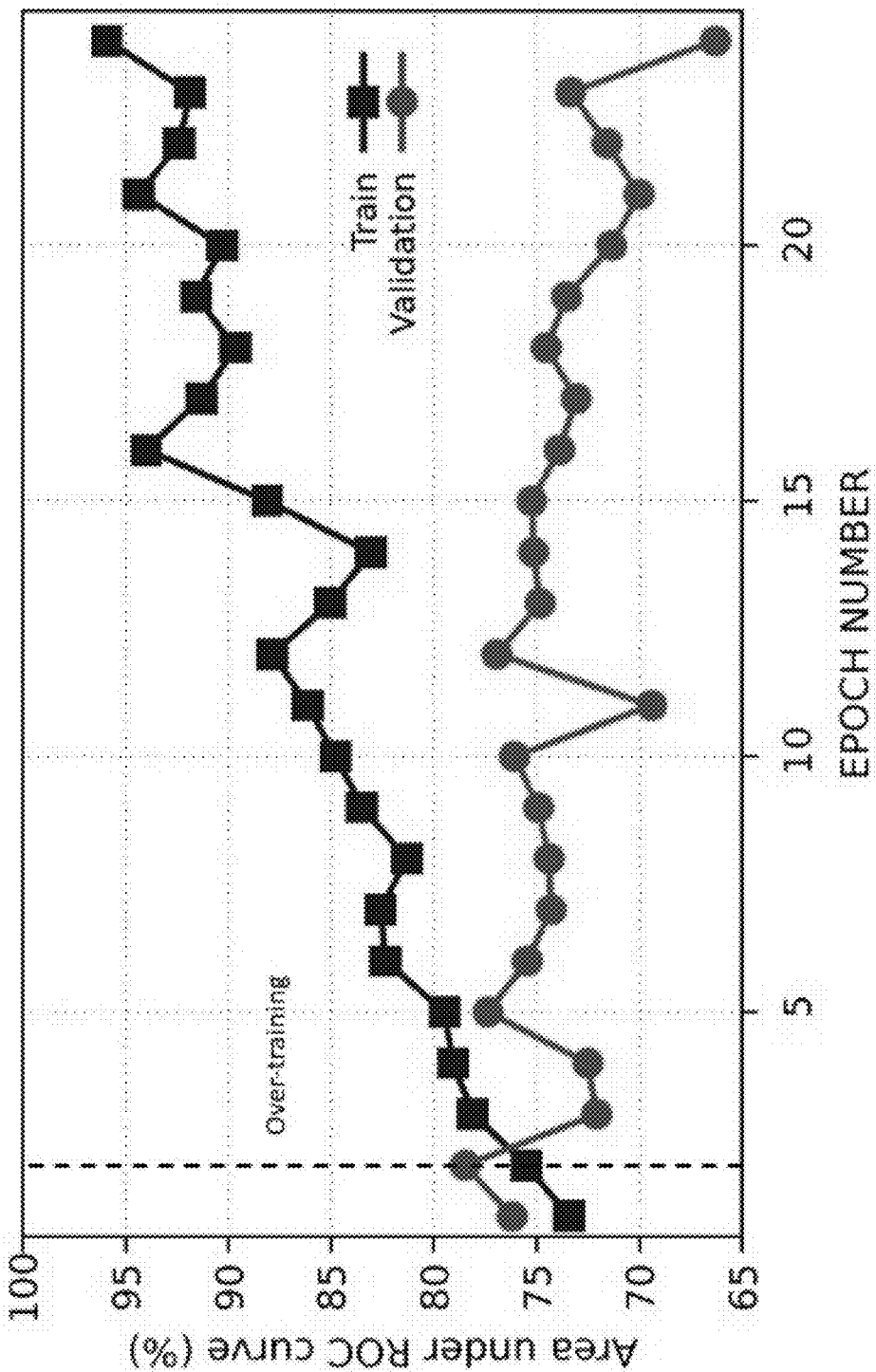
FIG. 13 is a graph illustrating performance on training and validation sets at each epoch for the target's baseline model.

It is visible from FIG. 13 that the model's performance on train and validation sets start to diverge after the second epoch. This epoch is chosen as the optimum epoch and the results for this model are evaluated in Table 7, which is shown in FIG. 14.

Figure 15:
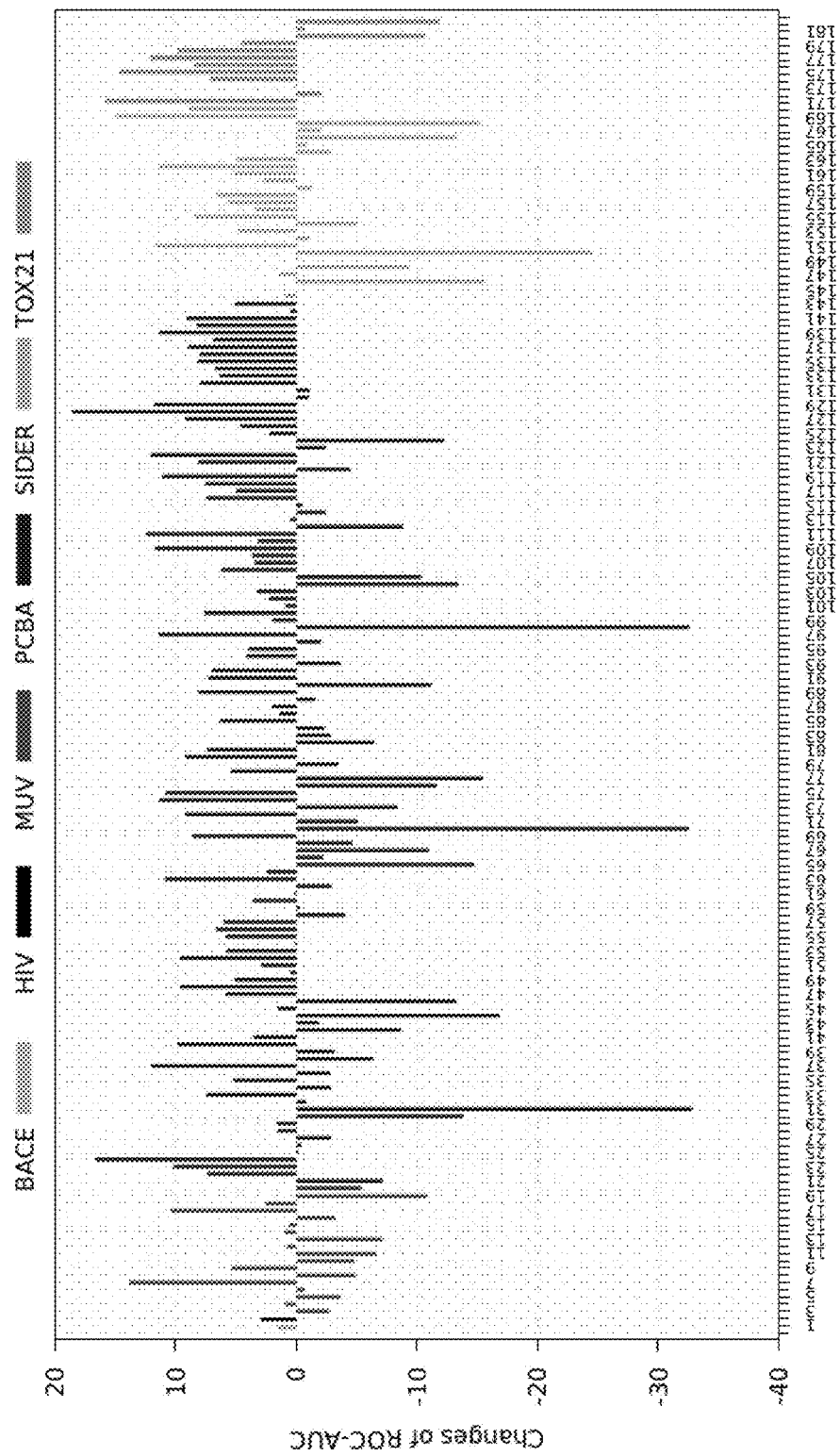
FIG. 15 illustrates the change in performance and the area under receiver operating curve (ROC-AUC) of model after transfer learning.

Transfer Learning Results 182 different source models from 6 datasets are trained for 30 epochs and then fine-tuned using the target dataset. The change in the ROC-AUC of the model on the target test set is depicted in FIG. 15. These results can also be seen in further details in FIG. 23.

Figure 16:
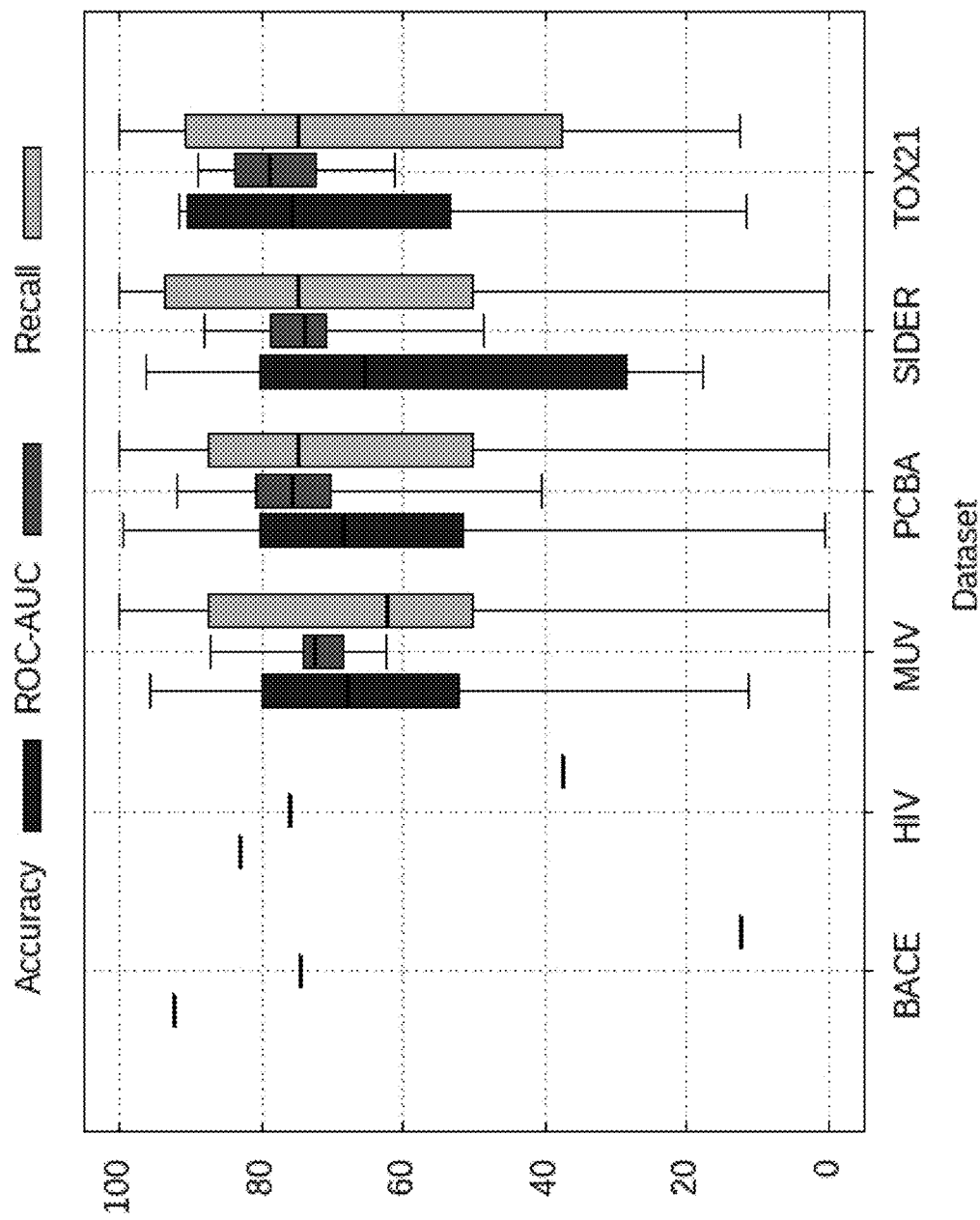
FIG. 16 illustrates the average change in performance and ROC-AUC of after transfer learning from each dataset.

As it is visible from FIG. 15, models within the same datasets can either improve or worsen the performance of the target model. The average outcome of these models in regards to the source datasets are shown in FIG. 16. The histogram of these results can be found in FIG. 25.

FIG. 16 demonstrates that on average, models transferred from the Tox21 dataset tend to perform well on the target task (highest average ROC-AUC), while the best and worst performing models originate from the PCBA dataset. The best performing models from each source task are shown in Table 8, which is shown in FIG. 17.

Figures 18A, 18B:
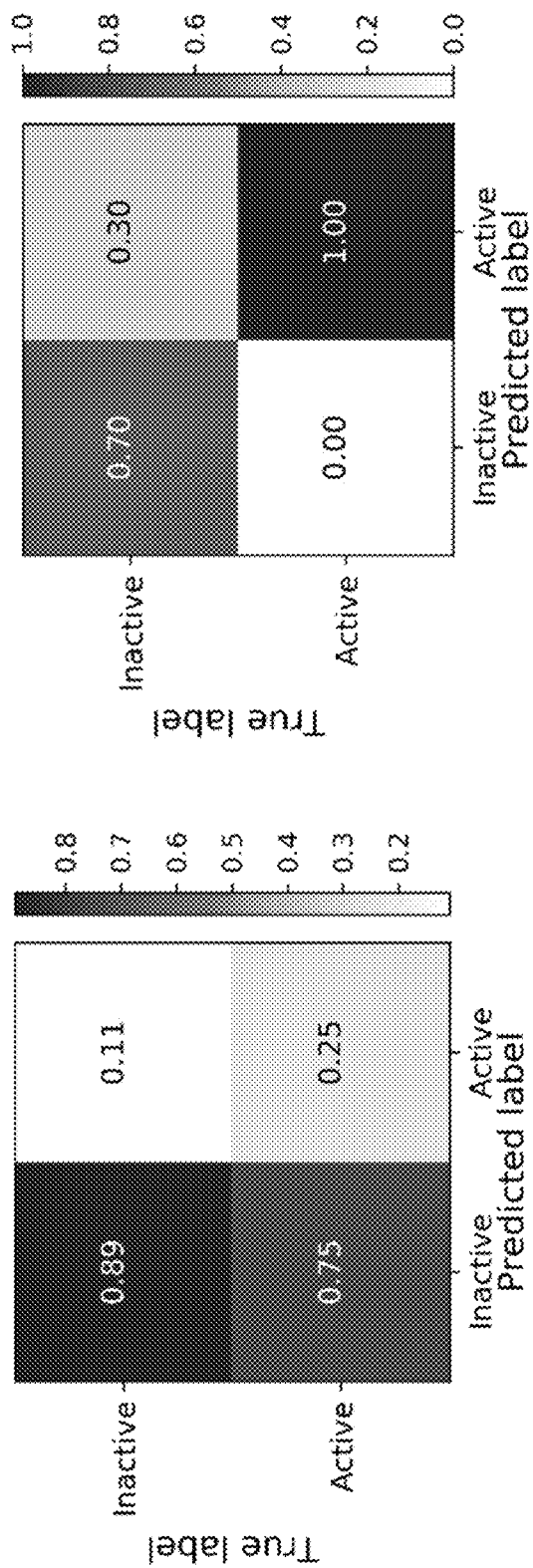

The overall best performing model is the model pre-trained on PCBA-651635 dataset and fine-tuned on the target dataset. This model also outperforms the state-of-the-art [18], which uses reinforcement learning from a related task to learn the target task. The best model's confusion matrix is compared to the baseline model in FIGS. 18A-18B, showing noticeable improvement in correctly predicting bio-active molecules after transfer learning. The ROC curves for these two models can be viewed in FIGS. 24A-24B.

Inter-Dataset Similarity Results

Figure 19:
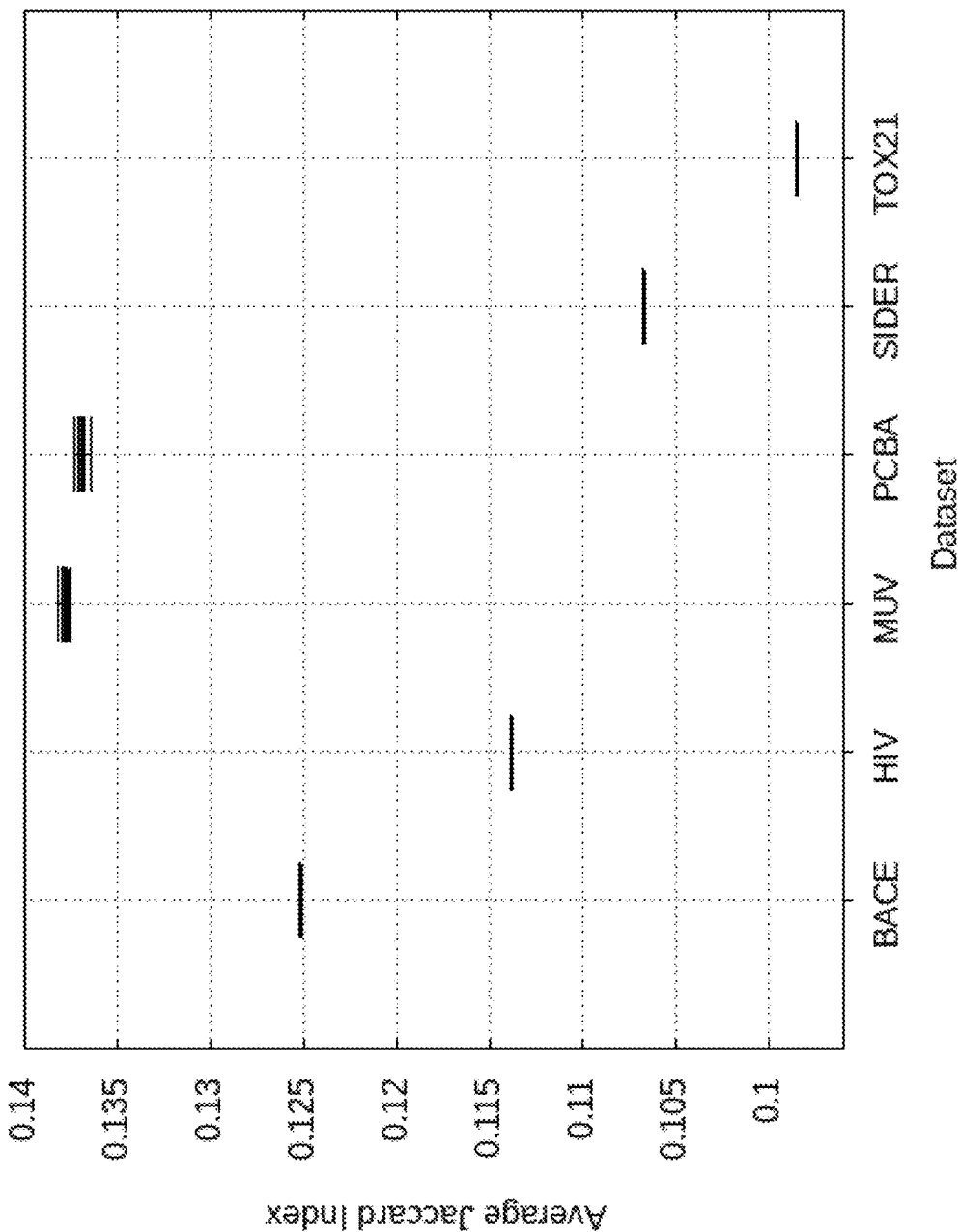
FIG. 19 illustrates similarity between each source dataset and the target dataset. Higher Jaccard Index indicates higher degree of similarity between the molecules.

The molecules within each source dataset are compared with those of the target dataset using Jaccard Index. The results are illustrated in FIG. 19, showing that the Tox21 and SIDER datasets are the most different data from the target dataset, with PCBA and MUV having high similarities to the target dataset.

Mean Silhouette Coefficient Results

Figure 20:
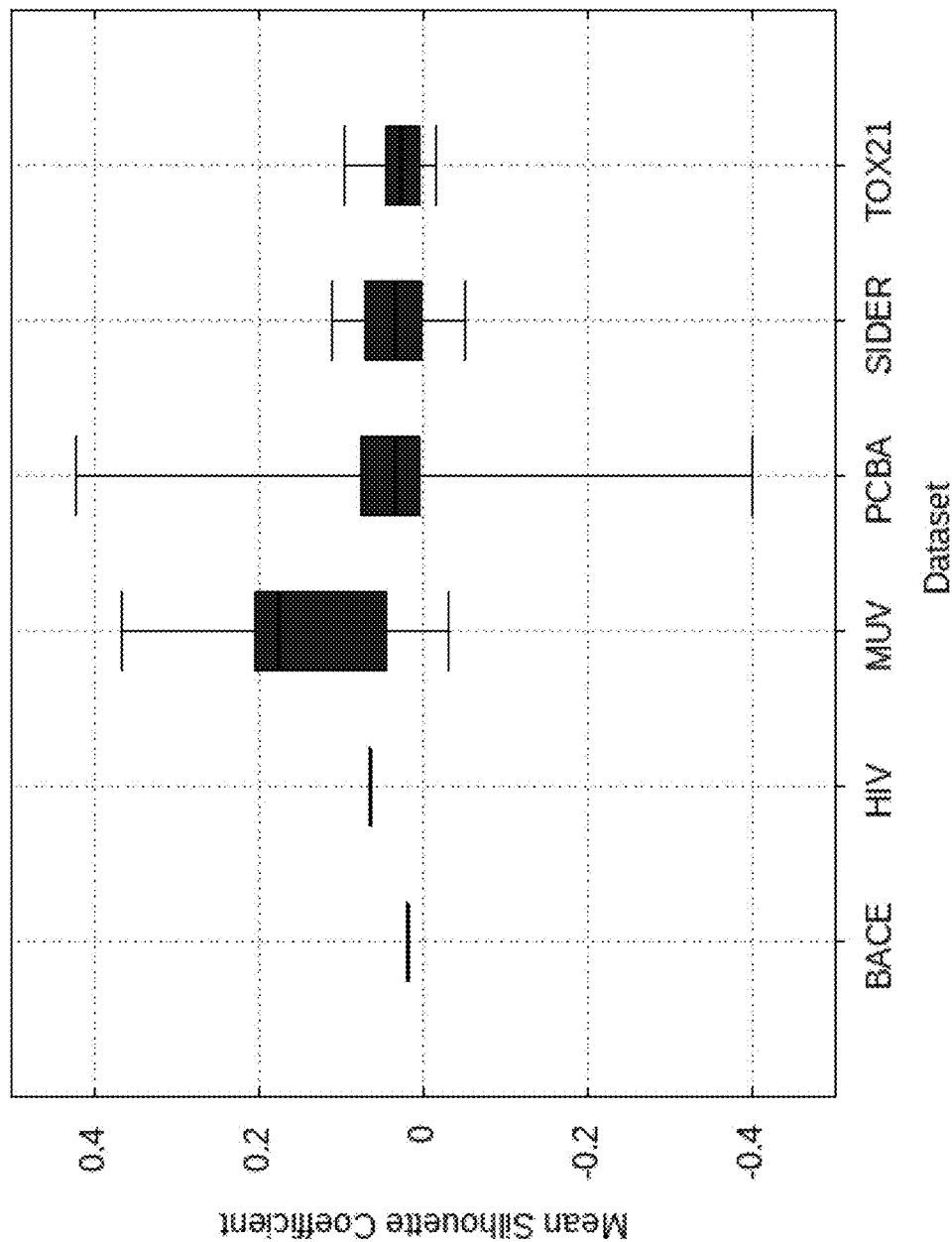
FIG. 20 illustrates Mean Silhouette Coefficient (MSC) between each source dataset and target datasets. Higher MSC indicates more distinguishable clusters formed from bio-active and inactive molecules.

The target validation dataset is fed to the pre-trained models and deep features are extracted from the second to last layer. The MSC of these features between active and inactive clusters are shown in FIG. 20, demonstrating that on average MUV has a higher capability of distinguishing between the target molecules. Moreover, PCBA contains tasks that possess the best and worst MSC scores.

Zero-Shot Inference Results

Figure 21:
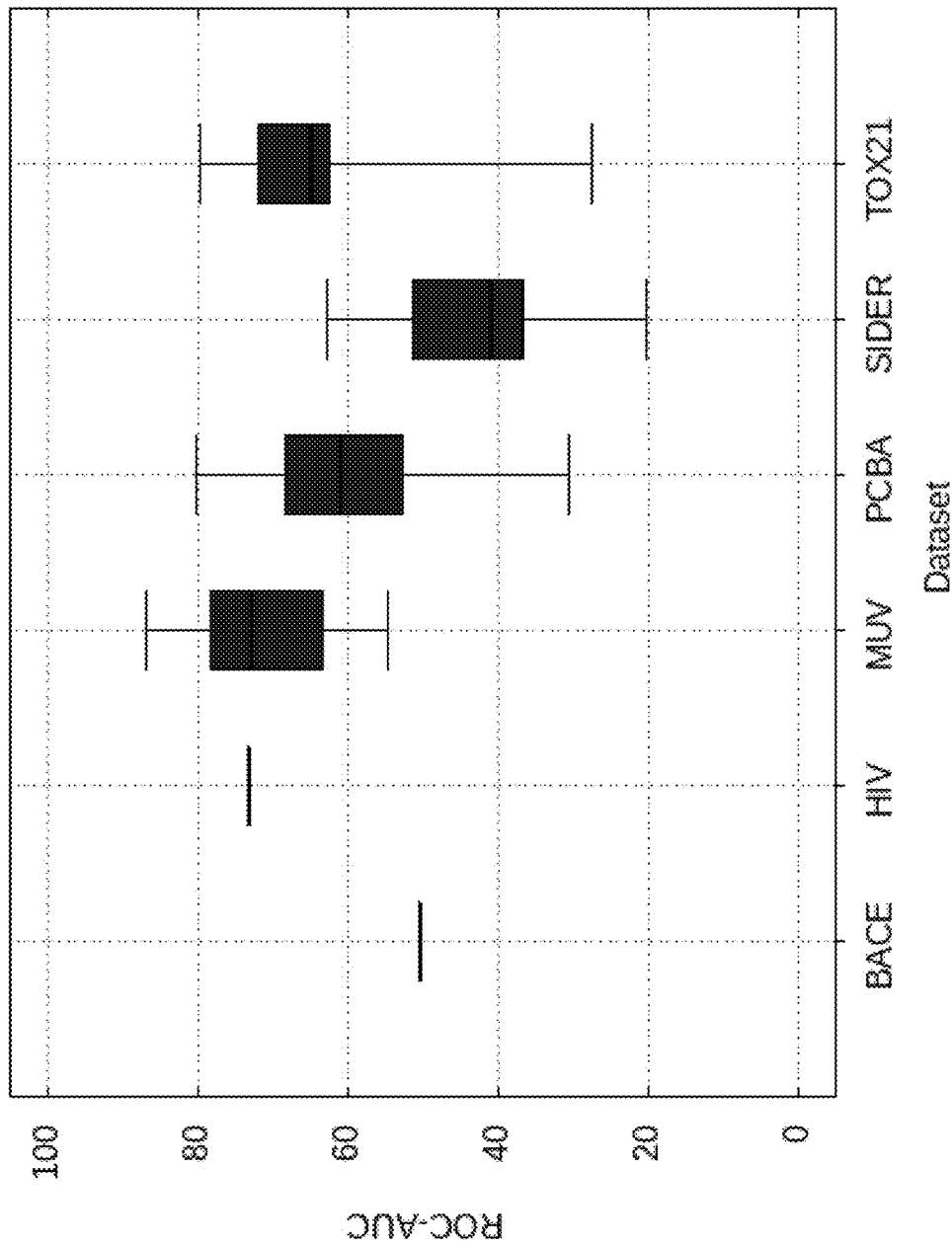
FIG. 21 illustrates performance of pre-trained models inferring on target validation set without fine-tuning. Higher ROC-AUC indicates better zero-shot inference.
Figure 23:
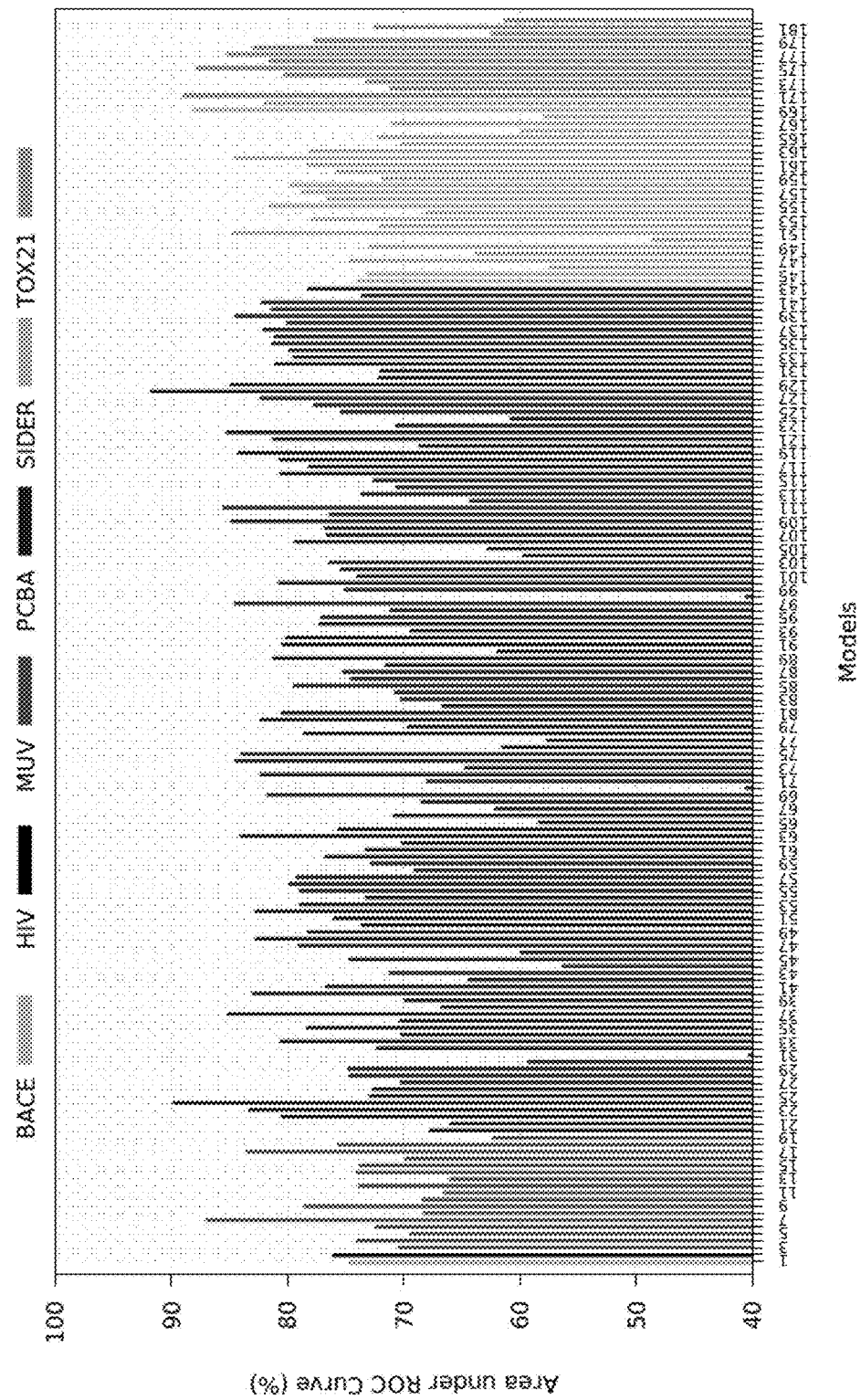
FIG. 23 illustrates detailed results of transfer learning from each source model after fine-tuning on the target dataset.
Figure 24B:
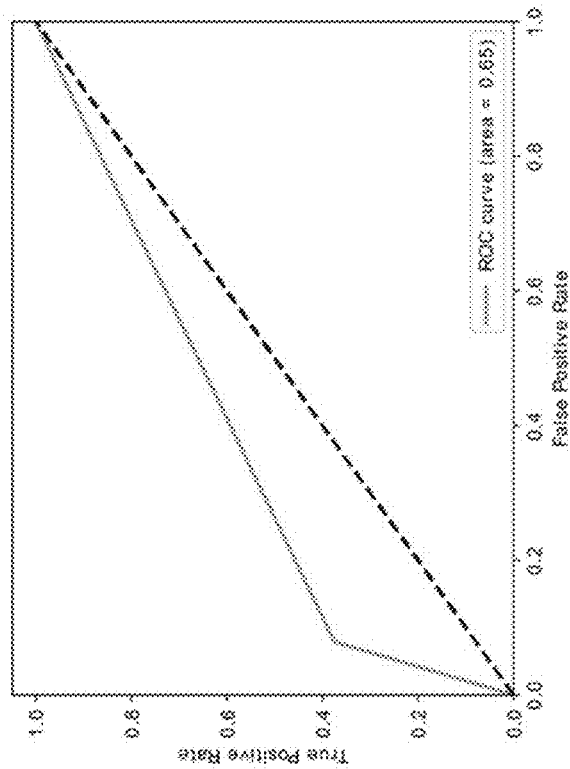
Figure 24A:
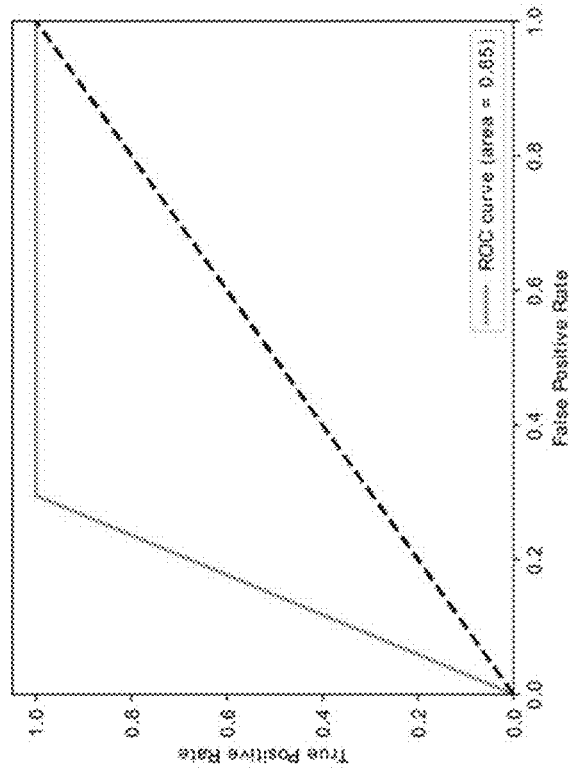
Figure 25:
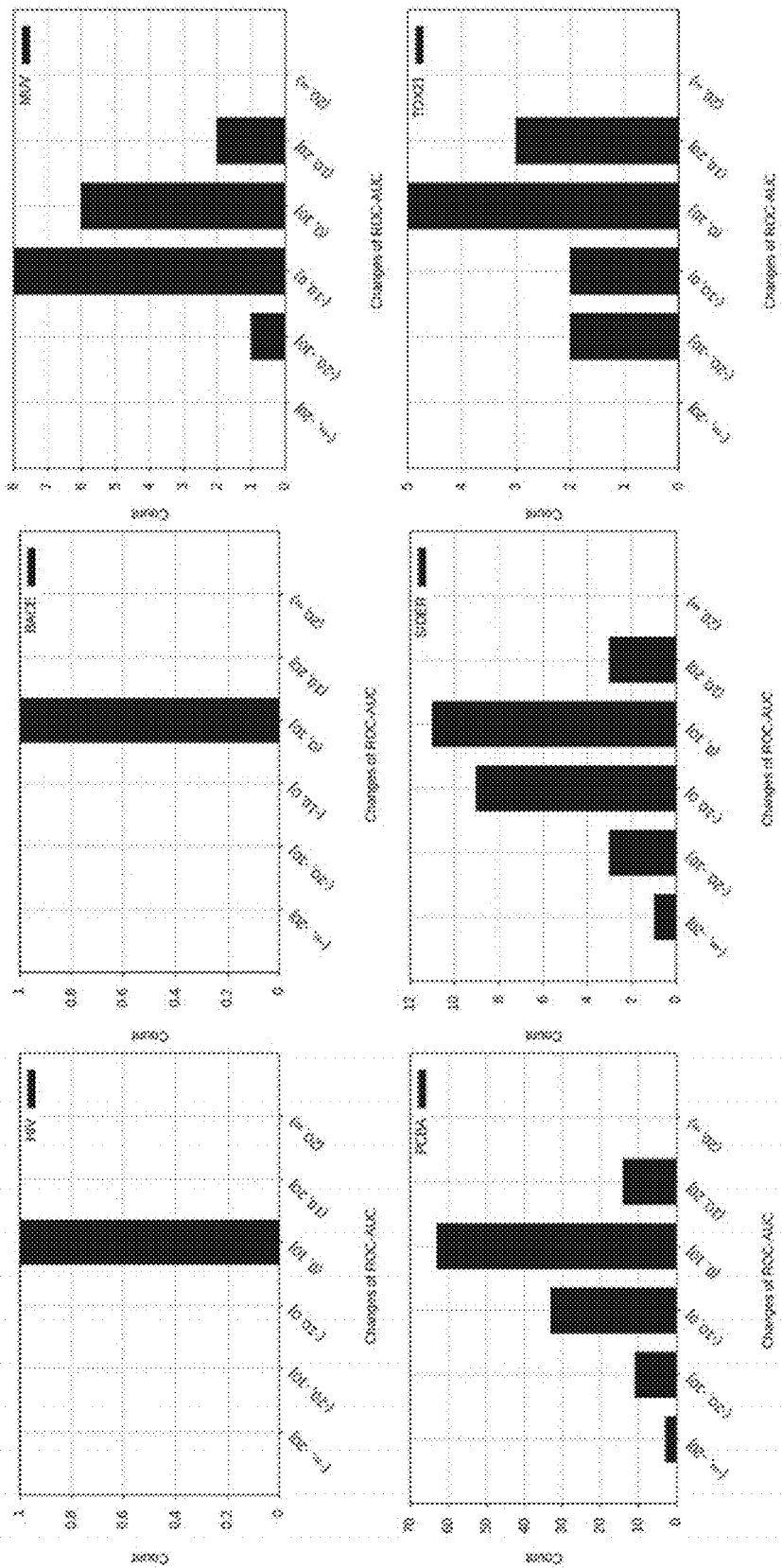
FIG. 25 illustrates histograms of the ROC-AUC improvements for each source model after fine-tuning on the target dataset.
Figure 26:
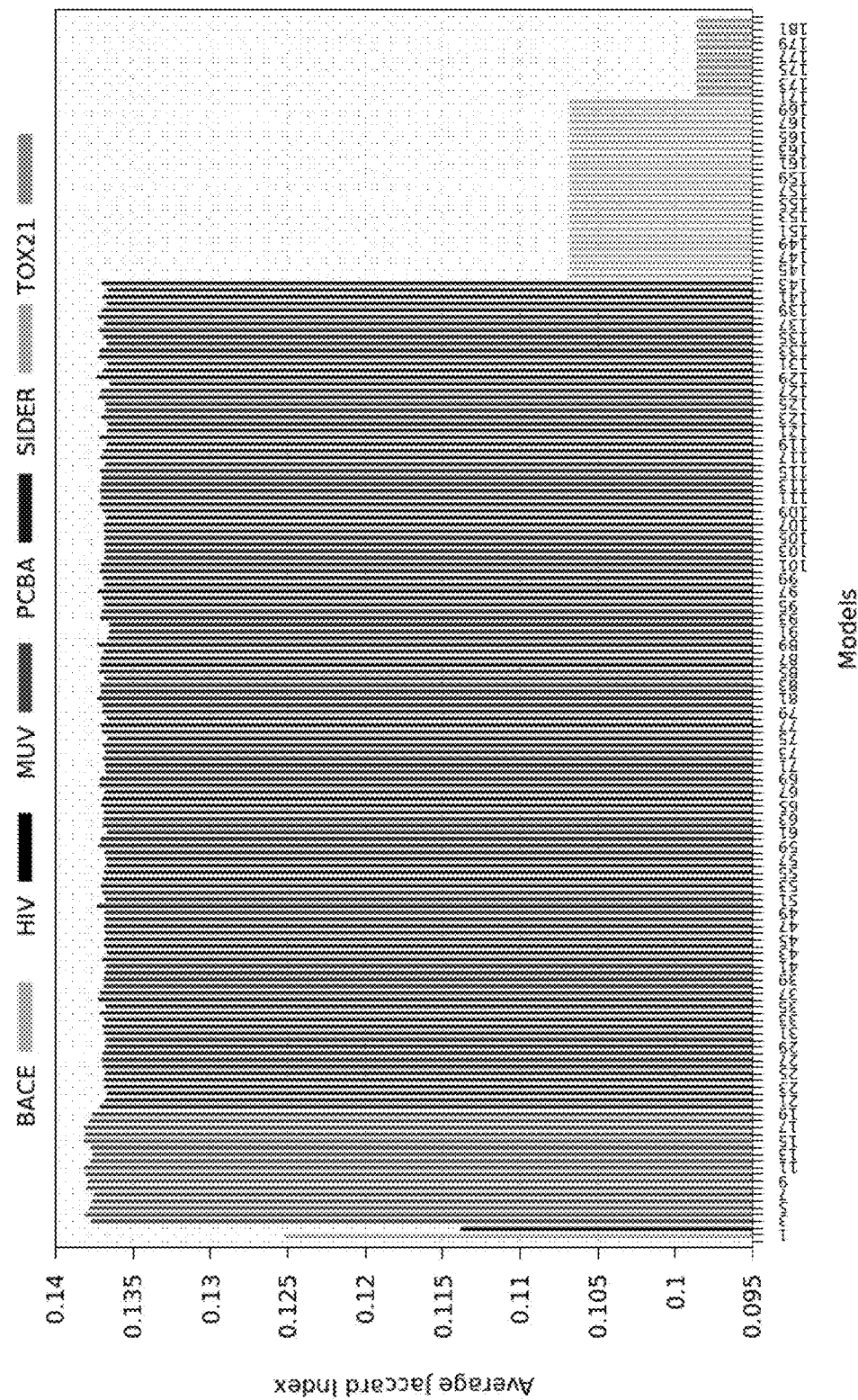
FIG. 26 illustrates detailed similarity of each source dataset to the target dataset.
Figure 27:
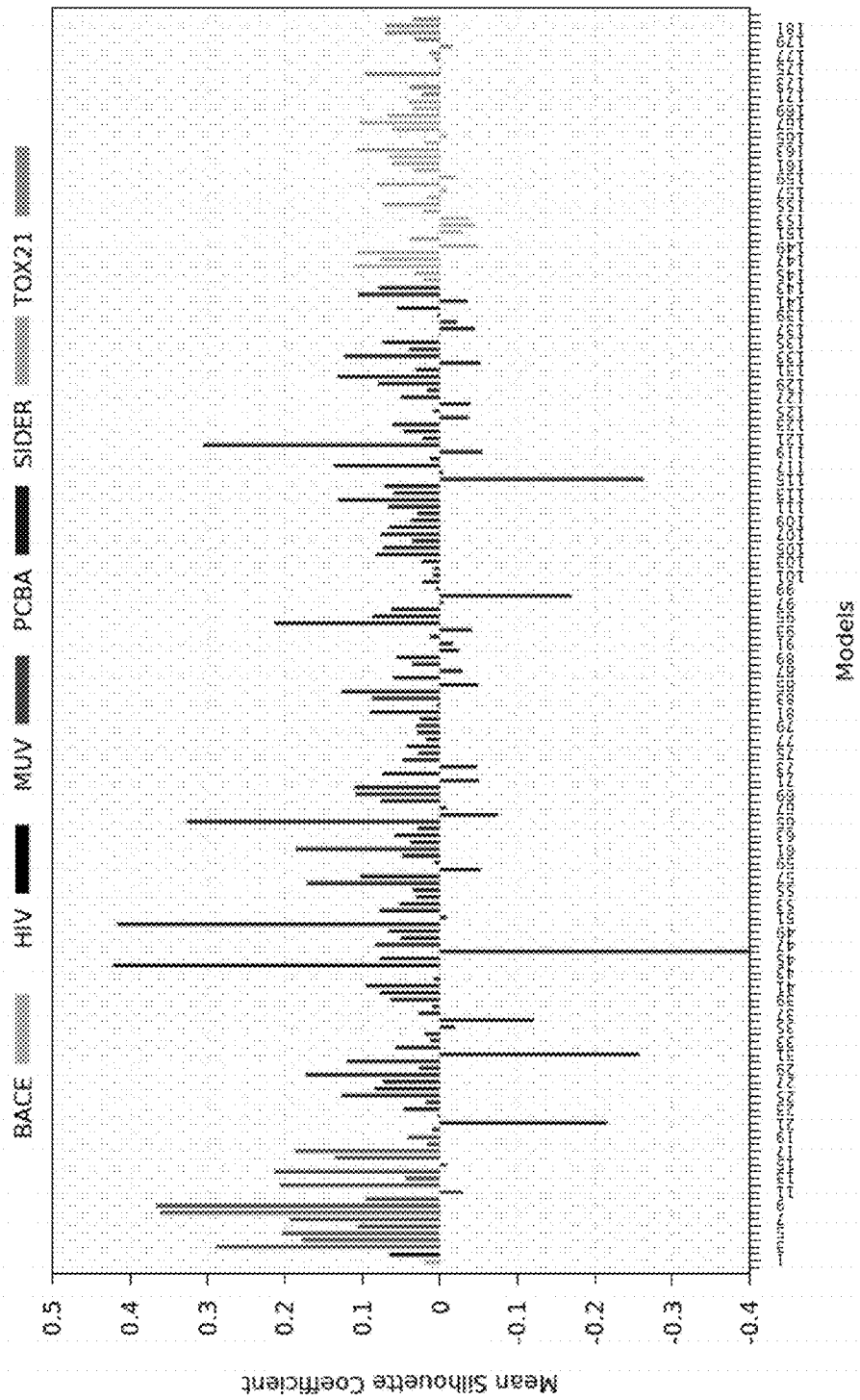
FIG. 27 illustrates discriminative capability (MSC) of each pre-trained source model in regards to the bio-activity of the target dataset's molecules.
Figure 28:
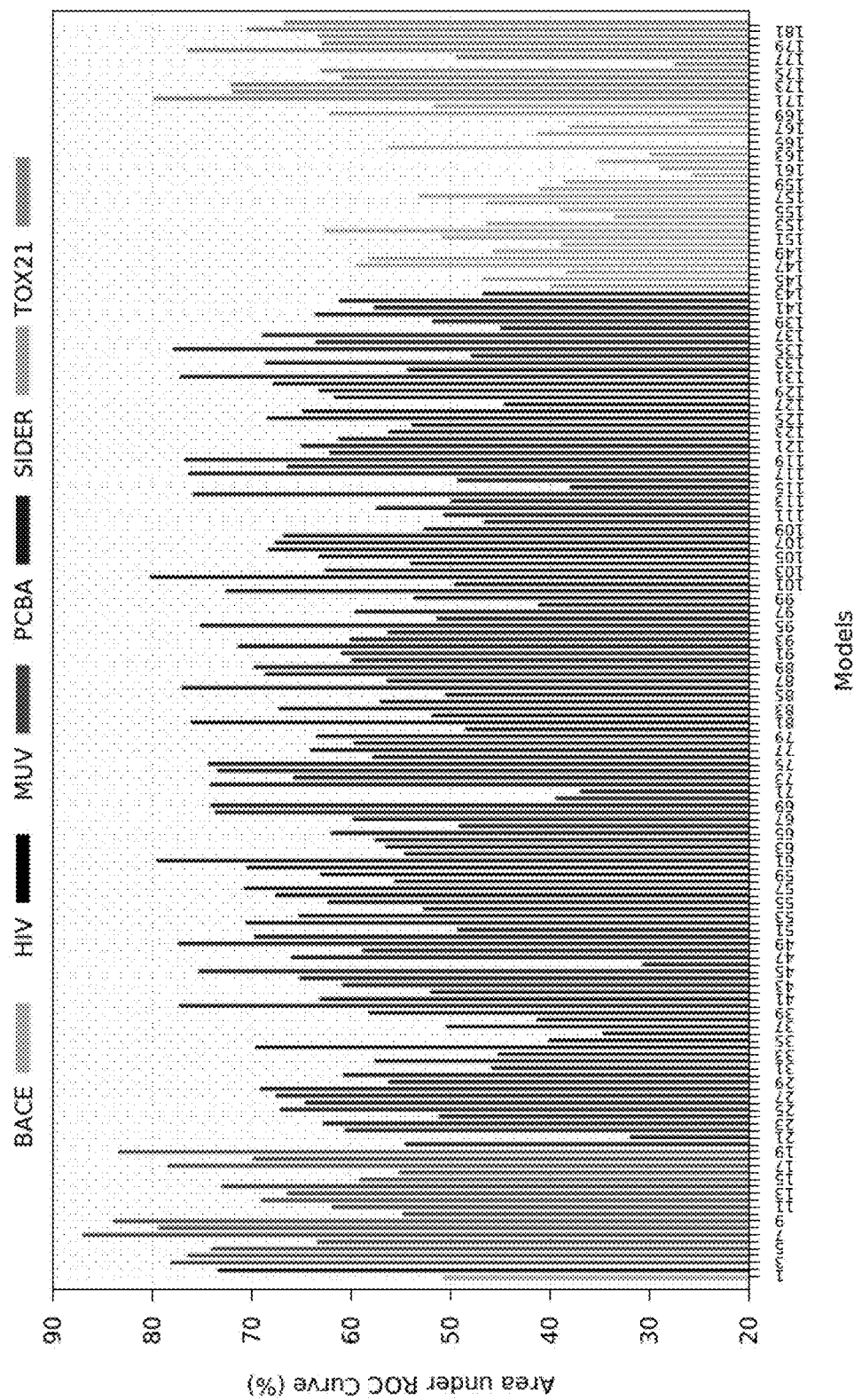
FIG. 28 illustrates detailed performance of pre-trained models inferring on target validation set without fine-tuning. (Correlation to improvement: 0.22).
Figure 29:
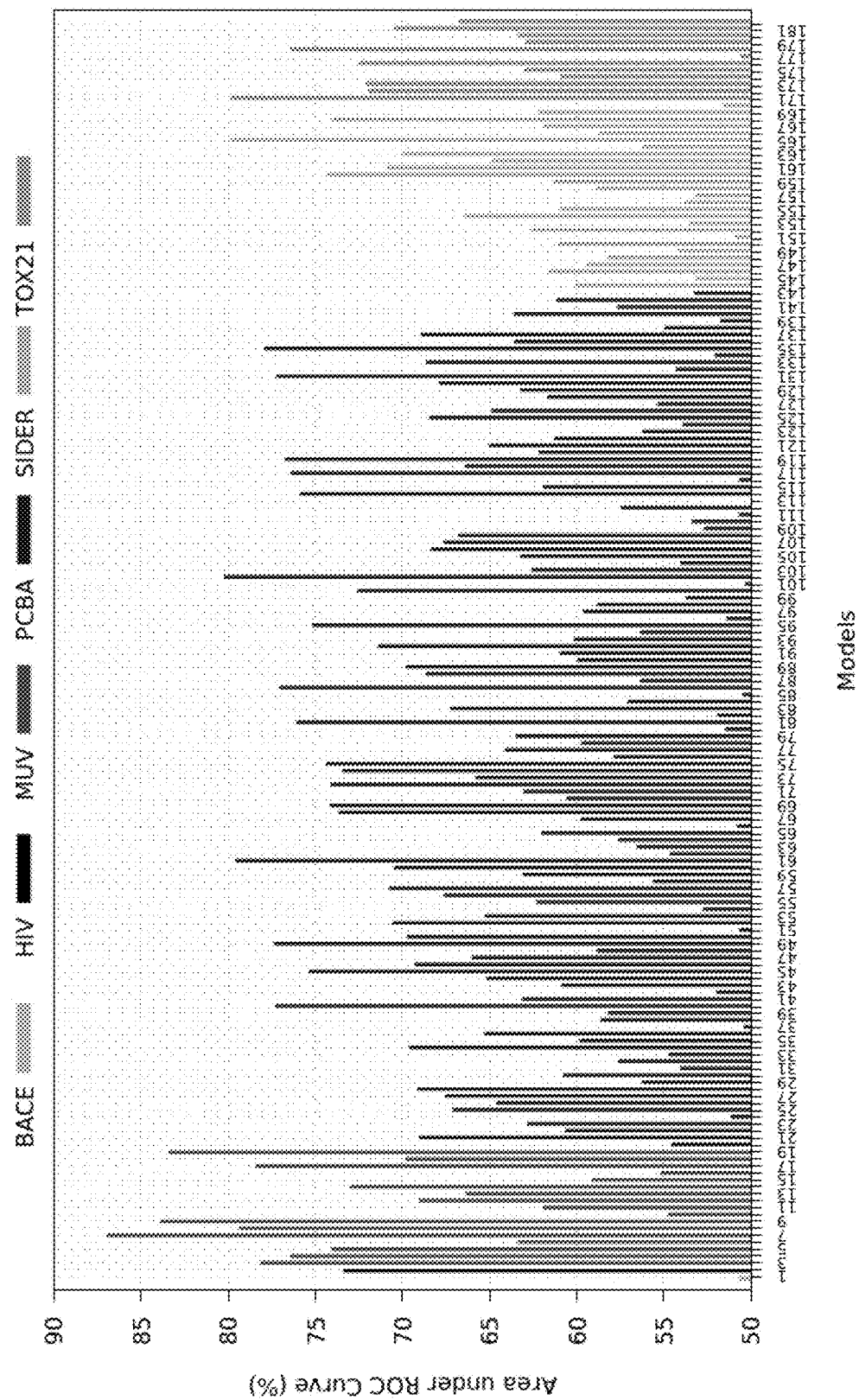
FIG. 29 illustrates detailed performance of pre-trained models inferring on target validation set without fine-tuning, results smaller than 0.5 are flipped to be larger than 0.5. (Correlation to improvement: 0.08).

The target validation set is given to pre-trained models in order to be classified solely based on the knowledge gained from the source data and with no fine-tuning on the target data. The results are shown in FIG. 21, demonstrating that MUV, Tox21, and PCBA are able to perform well on average through zero-shot inference.

Model Rank Prediction Results

After the results are acquired from three ranking approaches, the correlations between the results and the improvements in ROC-AUC of the test set are calculated. Furthermore, the number of correct top 10 predictions and their respective MRRs are calculated and reported in Table 9, which is shown in FIG. 22. IDS and MSC provided ranking predictions that were impractical for our target dataset. Zero-shot inference offers an improvement over previous approaches and can recommend two of the top ten models without performing fine-tuning.

Discussion and Results Interpretation

The baseline model for the target task shows clear signs of over-fitting at early stages of training, making it a prime candidate for performance improvement via better initialization. After transfer learning implementation, different initializations deliver varying performance and looking at three datasets in particular, enables better interpretation of the results:

PCBA: This dataset is one of the closest and most similar (in terms of fingerprint similarity) to the target dataset. It has the highest MSC, indicating that deep features learned from this data source can distinguish between active and inactive molecules. The best performing data source belongs to this dataset. However, it also possesses the tasks that yielded the lowest MSC and the worst performance.

MUV: This dataset is also very similar to the target dataset. On average the models trained on this dataset delivered the highest MSC. However, on average these models yielded the lowest performance improvement.

Tox21: This dataset is the most dissimilar to the target dataset. It does not perform well when tested with MSC measurement. However, the models from this dataset deliver the highest average improvement after transfer learning.

From the cheminformatics point of view, these results demonstrate the insufficiency of molecular similarity and bio-activity clusterization for a performance's prediction. In a non-structural, non-target-based virtual approach, the molecular data itself plays a very important role since there is no information regarding the target and its 3D structure. Therefore, similarity search and clustering would be a good approach to analyze data and to improve the performance. However, the first interpretation shows that a similarity search can even play an opposite role. In other words, the first interpretation is that judging by the training dataset or deep feature discrimination alone is not enough to understand the behavior of the model. These results demonstrate the fact that similar source dataset (to the target dataset) can perform poorly while dissimilar source datasets can give a high performance on average. Thus, refuting the traditional intuition that the source and target datasets should necessarily be similar. Deep feature discrimination did not prove to be fully capable of explaining the models' behavior either, since models with the highest MSC still could perform rather poorly on the target dataset. This is aligned with the literature, since ranking prediction is still an unsolved task and the prediction accuracy of these approaches varies between datasets and is averaged at 7% [41].

The second interpretation is that zero-shot inference reveals more information from the model and the underlying training data, which in turn delivers a better understanding of the model's behavior. The main difference between the proposed approach and the previous ones is examining how well the model can predict bio-activity of the molecules. Zero-shot inference includes information about target labels and the non-linearity of the last layer of the network into the ranking process, thus examining the model from more aspects. This can be seen in the fact that zero-shot inference offered better understanding of the Tox21 models' behavior and a better perspective for inspecting the model.

Conclusion

Graph convolutional neural networks have improved the accuracy of virtual screening models, yet face the challenge of imbalanced, non-diverse, and small training datasets. In this work the TranScreen pipeline is designed and implemented to alleviate these challenges with the help of diverse weight initialization. Transfer learning is utilized from 182 source models trained on the MoleculeNet database. The models are then fine-tuned on an anticancer prediction task. The results show that some source models can significantly improve the performance of the baseline target model, with the best model achieving 0.92 ROC-AUC and 100% recall. A collection of the pre-trained models is curated and made available for future virtual screening tasks to be used as weight initialization. Moreover, three approaches are implemented to rank and recommend pre-trained models for a given task, which also gave insight to how the models behave in regards with the training data and feature representations.

Appendix A

Cancer is a leading cause of death globally, ranking first or second for deaths in ages below 70 in the majority of countries [45]. This predominant contribution to global mortality, in addition to a significant economic burden [46], places cancer research in a place of paramount importance. In essence, the term "cancer" refers to a family of diseases that arise from abnormal cell growth; this abnormal growth occurs as a result of several cellular changes, usually triggered by mutations in the genome. At their root, many mutations and epigenetic changes can be traced to lifestyle and environmental factors, such as the use of tobacco products, alcohol intake, diet, exercise, and exposure to carcinogens and radiation; still other cancers are the result of inherited mutations and infections. The formation of tumors is a multistep process, characterized by several cellular "hallmarks of cancer", including sustained proliferative signaling, evasion of growth suppressors, resistance to cell death, enabled replicative immortality, induction of angiogenesis, and activation of invasion and metastasis; these characteristics are fueled by both genomic instability and inflammation [47]. The body employs several mechanisms to protect against cancer formation, known as "immunosurveillance", while tumors also evolve to avoid detection and clearance, via immune evasion [48]. The threshold between benign and malignant tumors is defined by migration of the tumor cells to a different location in the body, known as metastasis; this transition involves dedifferentiation of the cells into a stem-like migratory phenotype, and is associated with complication of treatment [49]. Traditional cancer treatment strategies involve surgical removal of tumors, radiotherapy, hormone therapy, and chemotherapy, while newer approaches include immunotherapy and targeted therapies. Targeted therapy differs from traditional chemotherapy in that it focuses on cancer-specific molecules, rather than acting on general cellular processes [50].

One of the ways to view cancer on a cellular level is as an imbalance of oncogenes, which can promote cancer; and tumor-suppressor genes (TSG), which work to prevent it [51]. Mutations in TSGs can lead to inhibition of their normal cancer-surveilling activity, allowing tumorigenesis to go unchecked [52]. One of the most important TSGs is TP53, which encodes the p53 protein, sometimes referred to as the "guardian of the genome" [53]. P53 is activated in response to stressors like DNA damage and deregulated growth, which can lead to cancer if unaddressed; such signals activate sensors like ATM/ATR and ARF, respectively, which then activate p53 via phosphorylation [54]. Once activated, p53 acts as a transcription factor, inducing transcription of genes that facilitate DNA damage repair, entrance into senescence (dormancy), or cell-mediated death (apoptosis), removing the potential for tumor formation [55]. P53's large role in tumor prevention can also be a weakness; cells with mutations in p53 are extremely vulnerable to transformation to a cancer state. Mutations in TP53 frequently interfere with p53's DNA-binding activity in its role as a transcription factor [56]. Current approaches to cancer therapy that target p53 focus on restoration of wild-type p53 functionality, removal of mutant p53, and inhibition of downstream pathways of mutant p53 [57]. Loss of normal function allows damaged cells to proliferate and mutate further, contributing to tumor formation and metastasis [58]. Not all biomolecules enhancing the carcinogenicity after p53 loss of function are yet discovered. Consequently, it has been challenging to discover molecules with unknown target of interest as anticancer. One way to do so would be prediction using non-target-based models [27], which is the main approach taken in this work.

REFERENCES

[1] Carnero, A. High throughput screening in drug discovery. *Clin. Transl. Oncol.* 2006, 8, 482-490.

[2] Mohs, R. C.; Greig, N. H. Drug discovery and development: Role of basic biological research. *Alzheimer's Dement.* (N.Y.) 2017, 3, 651-657. (In English)

[3] Miljković, F.; Rodríguez-Pérez, R.; Bajorath, J. Machine Learning Models for Accurate Prediction of Kinase Inhibitors with Different Binding Modes. *J. Med. Chem.* 2019.

[4] Sánchez-Rodríguez, A.; Pérez-Castillo, Y.; Schürer, S.C.; Nicolotti, O.; Mangiatordi, G. F.; Borges, F.; Cordeiro, M. N. D.; Tejera, E.; Medina-Franco, J. L.; Cruz-Monteagudo, M. From flamingo dance to (desirable) drug discovery: A nature-inspired approach. *Drug Discov. Today* 2017, 22, 1489-1502.

[5] Cruz-Monteagudo, M.; Ancede-Gallardo, E.; Jorge, M.; Cordeiro, M. N. D. S. Chemoinformatics Profiling of Ionic Liquids—Automatic and Chemically Interpretable Cytotoxicity Profiling, Virtual Screening, and Cytotoxicophore Identification. *Toxicol. Sci.* 2013, 136, 548-565.

[6] Perez-Castillo, Y.; Sánchez-Rodriguez, A.; Tejera, E.; Cruz-Monteagudo, M.; Borges, F.; Cordeiro, M. N. D.; Le-Thi-Thu, H.; Pham-The, H. A desirability-based multi objective approach for the virtual screening discovery of broad-spectrum anti-gastric cancer agents. *PLoS ONE* 2018, 13, e0192176.

[7] Korotcov, A.; Tkachenko, V.; Russo, D. P.; Ekins, S. Comparison of Deep Learning With Multiple Machine Learning Methods and Metrics Using Diverse Drug Discovery Data Sets. *Mol. Pharm.* 2017, 14, 4462-4475.

[8] Popova, M.; Isayev, O.; Tropsha, A. Deep reinforcement learning for de novo drug design. *Sci. Adv.* 2018, 4, eaap7885.

[9] Minnich, A. J.; McLoughlin, K.; Tse, M.; Deng, J.; Weber, A.; Murad, N.; Madej, B. D.; Ramsundar, B.; Rush, T.; Calad-Thomson, S.; et al. AMPL: A Data-Driven Modeling Pipeline for Drug Discovery. *J. Chem. Inf. Model.* 2020, 60, 1955-1968.

[10] Kearnes, S.; McCloskey, K.; Berndl, M.; Pande, V.; Riley, P. Molecular graph convolutions: Moving beyond fingerprints. *J. Comput. Aided Mol. Des.* 2016, 30, 595-608.

[11] Gimeno, A.; Ojeda-Montes, M. J.; Tomás-Hernández, S.; Cereto-Massagué, A.; Beltrán-Debón, R.; Mulero, M.; Pujadas, G.; Garcia-Vallvé, S. The Light and Dark Sides of Virtual Screening: What Is There to Know? *Int. J. Mol. Sci.* 2019, 20, 1375.

[12] Pérez-Sianes, J.; Pérez-Sánchez, H.; Díaz, F. Virtual Screening: A Challenge for Deep Learning. In *10th International Conference on Practical Applications of Computational Biology & Bioinformatics*; Springer International Publishing: Cham, Switzerland, 2016; pp. 13-22.

[13] Fischer, B.; Merlitz, H.; Wenzel, W. Increasing Diversity in In-silico Screening with Target Flexibility. In *Computational Life Sciences*; Springer: Berlin/Heidelberg, Germany, 2005; pp. 186-197.

[14] Hert, J.; Willett, P.; Wilton, D. J.; Acklin, P.; Azzaoui, K.; Jacoby, E.; Schuffenhauer, A. Comparison of Fingerprint-Based Methods for Virtual Screening Using Multiple Bioactive Reference Structures. *J. Chem. Inf. Comput. Sci.* 2004, 44, 1177-1185.

[15] Ramsundar, B.; Kearnes, S.; Riley, P.; Webster, D.; Konerding, D.; Pande, V. Massively multitask networks for drug discovery. arXiv 2015, arXiv:1502.02072.

[16] Altae-Tran, H.; Ramsundar, B.; Pappu, A. S.; Pande, V. Low Data Drug Discovery with One-Shot Learning. *ACS Cent. Sci.* 2017, 3, 283-293.

[17] Hu, W.; Liu, B.; Gomes, J.; Zitnik, M.; Liang, P.; Pande, V.; Leskovec, J. Strategies for Pre-training graph neural networks. arXiv 2019, arXiv:1905.12265.

[18] Liu, S. *Exploration on Deep Drug Discovery: Representation and Learning*; Computer Science, University of Wisconsin-Madison: Madison, WI, USA, 2018.

[19] Wu, Z.; Ramsundar, B.; Feinberg, E. N.; Gomes, J.; Geniesse, C.; Pappu, A. S.; Leswing, K.; Pande, V. MoleculeNet: A benchmark for molecular machine learning. *Chem. Sci.* 2018, 9, 513-530.

[20] Baugh, E. H.; Ke, H.; Levine, A. J.; Bonneau, R. A.; Chan, C. S. Why are there hotspot mutations in the TP53 gene in human cancers? *Cell Death Differ.* 2018, 25, 154-160.

[21] PubChem Database. Source=NCGC AID=904. 2007. Available online: https://pubchem.ncbi.nlm.nih.gov/bioassay/904 (accessed on 18 May 2020).

[22] Rogers, D.; Hahn, M. Extended-Connectivity Fingerprints. *J. Chem. Inf. Model.* 2010, 50, 742-754.

[23] Torng, W.; Altman, R. B. Graph Convolutional Neural Networks for Predicting Drug-Target Interactions. *J. Chem. Inf. Model.* 2019, 59, 4131-4149.

[24] Coley, C. W.; Jin, W.; Rogers, L.; Jamison, T. F.; Jaakkola, T. S.; Green, W. H.; Barzilay, R.; Jensen, K. F. A graph-convolutional neural network model for the prediction of chemical reactivity. *Chem. Sci.* 2019, 10, 370-377.

[25] Ramsundar, B.; Eastman, P.; Walters, P.; Pande, V.; Leswing, K.; Wu, Z. *Deep Learning for the Life Sciences*; O'Reilly Media: Sebastopol, CA, USA, 2019.

[26] Bjerrum, E. J. Smiles enumeration as data augmentation for neural network modeling of molecules. arXiv 2017, arXiv:1703.07076.

[27] Arshadi, A. K.; Salem, M.; Collins, J.; Yuan, J. S.; Chakrabarti, D. DeepMalaria: Artificial Intelligence Driven Discovery of Potent Antiplasmodials. *Front. Pharmacol.* 2019, 10, 1526.

[28] Devlin, J.; Chang, M.-W.; Lee, K.; Toutanova, K. Bert: Pre-training of deep bidirectional transformers for language understanding. arXiv 2018, arXiv:1810.04805.

[29] Nassif, A. B.; Shahin, I.; Attili, I.; Azzeh, M.; Shaalan, K. Speech Recognition Using Deep Neural Networks: A Systematic Review. *IEEE Access* 2019, 7, 19143-19165.

[30] Boumi, S.; Vela, A.; Chini, J. Quantifying the relationship between student enrollment patterns and student performance. arXiv 2020, arXiv:2003.10874.

[31] Zhang, K.; Guo, Y.; Wang, X.; Yuan, J.; Ding, Q. Multiple Feature Reweight DenseNet for Image Classification. *IEEE Access* 2019, 7, 9872-9880.

[32] Sun, Q.; Liu, Y.; Chua, T.-S.; Schiele, B. Meta-transfer learning for few-shot learning. In Proceedings of the IEEE Conference on Computer Vision and Pattern Recognition, Long Beach, CA, USA, 16-20 Jun. 2019; pp. 403-412.

[33] Liu, S.; Johns, E.; Davison, A. J. End-to-end multi-task learning with attention. In Proceedings of the IEEE Conference on Computer Vision and Pattern Recognition, Long Beach, CA, USA, 16-20 Jun. 2019; pp. 1871-1880.

[34] Zhuang, F.; Qi, Z.; Duan, K.; Xi, D.; Zhu, Y.; Zhu, H.; Xiong, H.; He, Q. A Comprehensive Survey on Transfer Learning. arXiv 2019, arXiv:1911.02685.

[35] Frankle, J.; Carbin, M. The lottery ticket hypothesis: Finding sparse trainable neural networks. arXiv 2018, arXiv:1803.03635.

[36] Fawaz, H. I.; Forestier, G.; Weber, J.; Idoumghar, L.; Muller, P. Transfer learning for time series classification. In Proceedings of the 2018 IEEE International Conference on Big Data (Big Data), Zurich, Switzerland Seattle, WA, USA, 10-13 Dec. 2018; pp. 1367-1376.

[37] Wang, M.; Deng, W. Deep visual domain adaptation: A survey. *Neurocomputing* 2018, 312, 135-153.

[38] Zhang, H.; Koniusz, P. Model Selection for Generalized Zero-Shot Learning. In *Computer Vision—ECCV 2018 Workshops*; Springer International Publishing: Cham, Switzerland, 2019; pp. 198-204.

[39] Zhang, H.; Koniusz, P. Zero-Shot Kernel Learning. In Proceedings of the 2018 IEEE/CVF Conference on Computer Vision and Pattern Recognition, Salt Lake City, Utah, USA, 18-22 Jun. 2018; pp. 7670-7679.

[40] Ben-David, S.; Blitzer, J.; Crammer, K.; Pereira, F. Analysis of representations for domain adaptation. In *Advances in NEURAL Information Processing Systems*; The MIT Press: Cambridge, MA, USA, 2007; pp. 137-144.

[41] Meiseles, A.; Rokach, L. Source Model Selection for Deep Learning in the Time Series Domain. *IEEE Access* 2020, 8, 6190-6200.

[42] Liu, S.; Alnammi, M.; Ericksen, S. S.; Voter, A. F.; Ananiev, G. E.; Keck, J. L.; Hoffmann, F. M.; Wildman, S. A.; Gitter, A. Practical Model Selection for Prospective Virtual Screening. *J. Chem. Inf. Model.* 2019, 59, 282-293.

[43] Swamidass, S. J.; Azencott, C.-A.; Lin, T.-W.; Gramajo, H.; Tsai, S.-C.; Baldi, P. Influence relevance voting: An accurate and interpretable virtual high throughput screening method. (in eng). *J. Chem. Inf. Model.* 2009, 49, 756-766.

[44] Zhang, H.; Koniusz, P. Power Normalizing Second-Order Similarity Network for Few-Shot Learning. In Proceedings of the 2019 IEEE Winter Conference on Applications of Computer Vision (WACV), Waikoloa Village, HI, USA, 7-11 Jan. 2019; pp. 1185-1193.

[45] Bray, F.; Ferlay, J.; Soerjomataram, I.; Siegel, R. L.; Torre, L. A.; Jemal, A. Global cancer statistics 2018: GLOBOCAN estimates of incidence and mortality worldwide for 36 cancers in 185 countries. *CA Cancer J. Clin.* 2018, 68, 394-424.

[46] Yabroff, K. R.; Warren, J. L.; Brown, M. L. Costs of cancer care in the USA: A descriptive review. *Nat. Clin. Pract. Oncol.* 2007, 4, 643-656.

[47] Hanahan, D.; Weinberg, R. A. Hallmarks of cancer: The next generation. *Cell* 2011, 144, 646-674.

[48] Smyth, M. J.; Dunn, G. P.; Schreiber, R. D. Cancer immunosurveillance and immunoediting: The roles of immunity in suppressing tumor development and shaping tumor immunogenicity. *Adv. Immunol.* 2006, 90, 1-50.

[49] Brabletz, T.; Jung, A.; Spaderna, S.; Hlubek, F.; Kirchner, T. Opinion: Migrating cancer stem cells—An integrated concept of malignant tumour progression. *Nat. Rev. Cancer* 2005, 5, 744-749.

[50] Huang, M.; Shen, A.; Ding, J.; Geng, M. Molecularly targeted cancer therapy: Some lessons from the past decade. *Trends Pharmacol. Sci.* 2014, 35, 41-50.

[51] Croce, C. M. Oncogenes and cancer. *N. Engl. J. Med.* 2008, 358, 502-511.

[52] Wang, L. H.; Wu, C. F.; Rajasekaran, N.; Shin, Y. K. Loss of Tumor Suppressor Gene Function in Human Cancer: An Overview. *Cell Physiol. Biochem.* 2018, 51, 2647-2693.

[53] Lane, D. P. Cancer. p53, guardian of the genome. *Nature* 1992, 358, 15-16.

[54] Ashcroft, M.; Taya, Y.; Vousden, K. H. Stress signals utilize multiple pathways to stabilize p53. *Mol. Cell Biol.* 2000, 20, 3224-3233.

[55] Oren, M. Decision making by p53: Life, death and cancer. *Cell Death Differ.* 2003, 10, 431-442.

[56] Goh, A. M.; Coffill, C. R.; Lane, D. P. The role of mutant p53 in human cancer. *J. Pathol.* 2011, 223, 116-126.

[57] Parrales, A.; Iwakuma, T. Targeting Oncogenic Mutant p53 for Cancer Therapy. *Front. Oncol.* 2015, 5, 288.

[58] Powell, E.; Piwnica-Worms, D.; Piwnica-Worms, H. Contribution of p53 to metastasis. *Cancer Discov.* 2014, 4, 405-414.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for training a graph convolutional neural network (GCNN) using transfer learning, the GCNN being configured for virtual screening of molecules for drug discovery, comprising:
receiving a first data set comprising a plurality of molecules and respective labels of a first target, wherein the molecules in the first data set are expressed in a computer-readable format;
training the GCNN to predict the first target to initialize one or more parameters of the GCNN using the first data set;
receiving a second data set, wherein the second data set comprises a plurality of molecules and respective labels of a second target, wherein the molecules in the second data set are expressed in the computer-readable format; and
training the GCNN to predict the second target to refine the one or more parameters of the GCNN using the second data set, wherein the molecules in the first data set are unrelated to the molecules in the second data set, wherein the first target is different than the second target, and wherein the second target is inhibition rate for a disease.

2. The method of claim 1, further comprising:
defining each of the molecules in the second data set by a plurality of selected features; and
converting the molecules in the second data set defined by the selected features into a plurality of respective graphs associated with each of the molecules, wherein training the GCNN to predict the second target to refine the one or more parameters of the GCNN comprises training the GCNN to predict the second target to refine the one or more parameters of the GCNN using the respective graphs.

3. The method of claim 2, wherein the selected features comprise a type of atom in a molecule, a degree of the atom, an implicit valence of the atom, hybridization of the atom, an aromatic property of the atom, a number of hydrogen atoms connected to the atom, or combinations thereof.

4. The method of claim 3, wherein the selected features further comprise chirality of the molecule.

5. The method of claim 1, further comprising optimizing a plurality of hyper-parameters of the GCNN, wherein the hyper-parameters comprises at least one of a number of convolution layers, a size of each convolution layer, a number of neurons in a dense layer, a dropout for each layer, a number of epochs, a learning rate, and a batch size.

6. The method of claim 5, wherein optimizing a plurality of hyper-parameters of the GCNN further comprises:
setting a plurality of respective values for each of the hyper-parameters;
for each respective value, training the GCNN using a set of molecules from the second data set and testing the GCNN using a third data set comprising a plurality of molecules, wherein the molecules in the third data set are expressed in the computer-readable format; and
selecting a set of respective values for each of the hyper-parameters, wherein the set of respective values for each of the hyper-parameters optimize performance of the GCNN.

7. The method of claim 6, further comprising augmenting the third data set to include additional copies of active molecules.

8. The method of claim 6, wherein the third data set comprises lab-validated data.

9. The method of claim 1, wherein the computer-readable format is simplified molecular input line entry system (SMILES) notation.

10. The method of claim 1, wherein the GCNN is configured for antimalarial drug discovery.

11. The method of claim 1, wherein the GCNN is configured for anticancer drug discovery.

12. A method for training a graph convolutional neural network (GCNN) using transfer learning, the GCNN being configured for virtual screening of molecules for drug discovery, comprising:
receiving a plurality of source data sets, each of the source data sets comprising a plurality of molecules and respective labels of a first target, wherein the molecules in each of the source data sets are expressed in a computer-readable format;

training a plurality of GCNNs to predict the first target to initialize one or more parameters of each of the GCNNs, wherein each of the GCNNs is trained using a respective one of the source data sets;

receiving a training data set, wherein the training data set comprises a plurality of molecules and respective labels of a second target, wherein the molecules in the training data set are expressed in the computer-readable format, wherein the molecules in the source data sets are unrelated to the molecules in the training data set, wherein the first target is different than the second target, and wherein the second target is inhibition rate for a disease; and training each of the GCNNs to predict the second target to refine the one or more parameters of each of the GCNNs using the training data set.

13. The method of claim 12, further comprising ranking each of the GCNNs trained using a respective one of the source data sets based on its respective predicted performance on the training data set.

14. The method of claim 13, wherein the step of ranking each of the GCNNs trained using a respective one of the source data sets based on its respective predicted performance on the training data set comprises analyzing a respective inter-dataset similarity between each of the source data sets and the training data set.

15. The method of claim 13, wherein the step of ranking each of the GCNNs trained using a respective one of the source data sets based on its respective predicted performance on the training data set comprises analyzing a respective ability of each of the GCNNs trained using a respective one of the source data sets to distinguish between active and inactive target molecules.

16. The method of claim 13, wherein the step of ranking each of the GCNNs trained using a respective one of the source data sets based on its respective predicted performance on the training data set comprises testing each of the GCNNs trained using a respective one of the source data sets using a validation data set.

17. The method of claim 12, wherein the source data sets have at least one of different data sizes, different data diversity, or different biological origin.

18. The method of claim 12, wherein each of the GCNNs is trained using a respective one of the source data sets for more epochs than each of the GCNNs is trained using the training data set.

19. A method for virtually screening molecules on *Plasmodium falciparum* (*P. falciparum*), comprising:

providing the GCNN trained according to claim 1;

receiving a molecule, wherein the molecule is expressed in a computer-readable format; and predicting, using the GCNN, whether the molecule inhibits *P. falciparum*.

20. The method of claim 19, further comprising classifying the molecule as an active molecule or an inactive molecule, wherein the active molecule is a drug candidate for treating *P. falciparum*.

* * * * *